US010264965B2

(12) United States Patent
Huang et al.

(10) Patent No.: US 10,264,965 B2
(45) Date of Patent: Apr. 23, 2019

(54) EYE IMAGING DEVICE AND METHOD OF USE

(71) Applicants: CAPITALBIO EHEALTH SCIENCE & TECHNOLOGY (BEIJING) CO., LTD., Beijing (CN); CapitalBio Corporation, Beijing (CN); Tsinghua University, Beijing (CN)

(72) Inventors: Guoliang Huang, Beijing (CN); Wenjun Wang, Beijing (CN); Hongmei Cao, Beijing (CN); Lili Zhang, Beijing (CN); Li Ma, Beijing (CN); Chengjin Zhang, Beijing (CN); Yimin Sun, Beijing (CN); Dong Wang, Beijing (CN); Jing Cheng, Beijing (CN)

(73) Assignee: CAPITALBIO EHEALTH SCIENCE & TECHNOLOGY (BEIJING) CO., LTD., Beijing (CN)

( * ) Notice: Subject to any disclaimer, the term of this patent is extended or adjusted under 35 U.S.C. 154(b) by 158 days.

(21) Appl. No.: 15/374,818

(22) Filed: Dec. 9, 2016

(65) Prior Publication Data

US 2017/0164830 A1 Jun. 15, 2017

(30) Foreign Application Priority Data

Dec. 9, 2015 (CN) .......................... 2015 1 0904265

(51) Int. Cl.
*A61B 3/12* (2006.01)
*A61B 3/15* (2006.01)
(Continued)

(52) U.S. Cl.
CPC ............ *A61B 3/156* (2013.01); *A61B 3/0025* (2013.01); *A61B 3/0058* (2013.01);
(Continued)

(58) Field of Classification Search
CPC ........... A61B 3/14; A61B 3/024; A61B 3/102; A61B 3/0008; A61B 3/1216
(Continued)

(56) References Cited

U.S. PATENT DOCUMENTS 9,610,010 B2 * 4/2017 Srivastava ........... A61B 3/0025
2017/0164830 A1 6/2017 Huang et al.

FOREIGN PATENT DOCUMENTS

| CN | 2906791 Y | 5/2007 |
| CN | 104768447 A | 7/2015 |
| WO | 2010051304 A1 | 5/2010 |

* cited by examiner

*Primary Examiner* — Hung X Dang
(74) *Attorney, Agent, or Firm* — Rimon, P.C.

(57) ABSTRACT

In one aspect, disclosed herein are devices, systems, and methods for assessing human health states based on non-shadow imaging of sclera, or whites, of one or both eyes. In one aspect, the device is an on-body device. In one aspect, the system comprises a positioning aperture, an illuminating apparatus, an imaging apparatus, and/or a processing apparatus. In one aspect, the process only takes a short period of time to take images of the sclera without any operation of splicing multiple images. In one aspect, the device or system improves the quality of images by avoiding the formation of reflection of the illuminating apparatus on the images of the sclera. In a further aspect, the system can utilize the sclera images to obtain information of eye diseases and to predict the physiological and pathological changes in the health status of subject or diagnostic results, which can provide helpful information for medical diagnosis.

22 Claims, 5 Drawing Sheets

(51) Int. Cl.
*G06F 16/51* (2019.01)
*G06F 16/583* (2019.01)
*G06T 7/13* (2017.01)
*A61B 3/00* (2006.01)
*G06K 9/00* (2006.01)
*G06K 9/46* (2006.01)
*G06T 7/00* (2017.01)

(52) U.S. Cl.
CPC .......... *A61B 3/0083* (2013.01); *A61B 3/0091* (2013.01); *G06F 16/51* (2019.01); *G06F 16/5838* (2019.01); *G06K 9/0061* (2013.01); *G06K 9/00604* (2013.01); *G06K 9/00617* (2013.01); *G06K 9/4604* (2013.01); *G06T 7/0012* (2013.01); *G06T 7/0014* (2013.01); *G06T 7/13* (2017.01); *G06K 2209/05* (2013.01); *G06T 2207/10004* (2013.01); *G06T 2207/10024* (2013.01); *G06T 2207/30041* (2013.01)

(58) Field of Classification Search
USPC .................. 351/206, 207, 214, 221, 246
See application file for complete search history.

EYE IMAGING DEVICE AND METHOD OF USE

CROSS-REFERENCE TO RELATED APPLICATIONS

This application claims priority to Chinese Patent Application No. 201510904265.9, filed on Dec. 9, 2015, the content of which is incorporated by reference herein in its entirety for all purposes.

TECHNICAL FIELD

The present disclosure relates to the field of optical imaging, and in particular aspects, to an on-body device or system for sclera imaging, and methods of using the device or system for analyzing human health and/or disease status, including but not limited to eye health and conditions, based on sclera images.

BACKGROUND

The eye is one of the important organs for humans to obtain outside information. The health of the eye is getting more and more attention. Regular examinations of the eye typically include anterior segment examination and/or fundus examination. The anterior segment examination includes examinations of the iris, pupil, sclera, and the like.

Some existing apparatuses or devices used for eye imaging, such as those disclosed in Chinese Patent Application No. 200620096156.5 and Chinese Patent Application No. 201380057539.4, have not solved the problem of the light source having a reflection on the sclera and therefore on the wide-field image of the sclera. Among similar devices and methods, the structure of the device disclosed in Chinese Patent Application No. 201380057539.4 is the most complicated and representative. That device, through a complex motor control device, guides a camera to track and image the eye surface or pupil in a three-dimensional movement (i.e., x-y-z axis) of the eye. The captured image from a given position of the camera is used to determine whether the image should be rejected due to the existence of a reflection on that image, or whether multiple images should be taken from that position. Upon detection of the presence of a reflective image at a spot or region of interest in the eye, the motor control device is required to adjust the position of a sight guidance system and the position of the camera. Through the adjustment, the spot or region of interest in the eye is moved away from the reflective image of the light source, and the eye is imaged again to avoid reflection of the light source and/or other artifacts associated with imaging, and to ensure the image quality of that particular spot or region in the eye that is expected to be monitored. Obviously, this method of adjusting the position of the sight guidance system and the camera by the motor control device to allow the particular spot or region in the eye to be away from the reflection image is not only troublesome in operation and time consuming, but also complicated in the structure of the control system device. Furthermore, the method does not fundamentally solve the problem caused by the reflection of the light source, and does not directly mitigate the impact of that reflection.

The device disclosed in Chinese Patent Application No. 201380057539.4 for imaging the eye at a particular point or region uses one camera right in front of the eye, which cannot capture a wide-field image of the sclera without reflections. Multiple cameras must be used to meet the requirement of imaging multiple points or regions in the eye to obtain quality images that are free from reflections of the light source and/or other artifacts during imaging. This is because none of the multiple cameras can perform, without interruption, a wide-field imaging of the entire sclera without light reflections. Rather, multiple cameras are used to each capture images of a part (a particular point or region) of a sclera, and then the individual images are edited through an image mosaic reconstruction method in order to obtain a larger wide-field image of the sclera without reflection of the light source. In sum, the whole process disclosed in Chinese Patent Application No. 201380057539.4 is time-consuming and troublesome and requires many steps of editing a large number of images.

Therefore, there is a need for an eye imaging analysis system which is fast in producing good quality images of the eye, such as a wide-field image of the sclera. The present disclosure addresses this and the related needs, such as analyzing the physiological and/or pathological changes of a subject in order to better meet the requirements of different areas of use, including prevention, diagnosis, treatment, and/or prognosis of a disease or condition.

SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

In one aspect, disclosed herein is a device for analyzing a sclera of a subject, comprising: a member comprising a positioning aperture for engaging an eye of a subject on one side of the positioning aperture, wherein the positioning aperture is on a plane and has a center; and a light source on the opposite side of the positioning aperture from the eye, wherein the line connecting the light source and the center of the positioning aperture intersects the plane at an angle of less than 90 degrees, wherein light from the light source, through the positioning aperture, obliquely illuminates the eye such that the reflection image of the light source is substantially outside of the sclera of the eye, whereby a sclera image is captured substantially without capturing the reflection image of the light source.

In one aspect, disclosed herein is a device for analyzing a sclera of a subject, comprising: a member comprising a positioning aperture for engaging an eye of a subject on one side of the positioning aperture, wherein the positioning aperture is on an imaginary plane and has a center; and a light source on the opposite side of the positioning aperture from the eye, wherein an imaginary connecting the light source and the center of the positioning aperture intersects the plane at an angle of less than 90 degrees, wherein light from the light source, through the positioning aperture, obliquely illuminates the eye such that the reflection image of the light source is completely outside of the sclera of the eye, whereby a sclera image is captured substantially without capturing any part of the reflection image of the light source.

In another aspect, disclosed herein is a device for analyzing a sclera of a subject, comprising: a member comprising a positioning aperture for engaging an eye of a subject on one side of the positioning aperture, wherein the positioning aperture comprises two horizontally (or left-right) symmetric eye positioning surfaces and two vertically (or up-down) symmetric holes for flipping the eyelids; and a light source on the opposite side of the positioning aperture from the eye, wherein an imaginary line connecting the light source and the center of the positioning aperture intersects the positioning aperture at an angle of less than 90 degrees, wherein light from the light source, through the positioning aperture, obliquely illuminates the eye such that the reflection image of the light source is completely outside of the sclera of the eye, whereby a sclera image is captured without capturing any part of the reflection image of the light source.

In some embodiments, the angle is an oblique angle for illumination. In one aspect, oblique illumination is a lighting technique that uses an illuminating beam of light that is directed onto a stage (e.g., where an object to be observed or imaged is located) at an oblique angle rather than a normal angle to the stage. In one aspect, oblique illumination has a number of very useful applications that result from the fact that the numerical aperture (NA) of the light source is greater than that of the objective (e.g., of a microscope) in one direction and may be less than that of the objective at right angles to the plane containing the incident beam axis and the normal to the stage. Using a microscope as an example, if the illuminating beam traverses the stage at an oblique angle from right to left then and the object on the stage is mounted in a medium of lower refractive index then the light at the right side of a transparent object will be refracted toward the center of the object. The result is that the beam is refracted at an angle that the objective can't collect. That side of the object will appear dark. The other side of the object will appear bright because refraction toward the center of the object brings more of the oblique light into an angle that can be collected by the objective.

In some embodiments, the device is an on-body device, for example, a wearable device. In some embodiments, the device is a mobile device.

In any of the preceding embodiments, the member comprising the positioning aperture can be an on-body member, for example, a wearable member. In some embodiments, the member comprising the positioning aperture is a mobile member.

In any of the preceding embodiments, the angle can be less than about 80 degrees, about 70 degrees, about 60 degrees, or about 50 degrees.

In any of the preceding embodiments, the angle can be less than about 45 degrees, about 40 degrees, about 35 degrees, about 30 degrees, about 25 degrees, about 20 degrees, about 15 degrees, about 10 degrees, or about 5 degrees.

In any of the preceding embodiments, all or part of the reflection image of the light source can be on the iris of the eye, for example, at least about 50%, about 60%, about 70%, about 80%, about 90%, about 95%, or about 99% of the area of the reflection image is on the iris of the eye. In any of the preceding embodiments, less than about 50%, about 40%, about 30%, about 20%, about 10%, about 5%, or about 1% of the area of the reflection image can be on the sclera of the eye.

In any of the preceding embodiments, the reflection image of the light source can be completely outside of the sclera of the eye. In any of the preceding embodiments, the sclera image can be captured without capturing any part of the reflection image of the light source.

In any of the preceding embodiments, the device can further comprise an imaging member for imaging the sclera of the eye, wherein the sclera image is a non-shadow, wide-field image.

In any of the preceding embodiments, the device can further comprise a processing member configured to connect to the imaging member, wherein the processing member stores the sclera image, extract a feature of the sclera image, compares the extracted feature with a reference or model in a database, and/or generates report of a health/disease status of the eye, a health/disease status of another organ or tissue of the subject, a physiological or pathological indicator of the subject, an overall health/disease status of the subject, and/or a diagnostic or prognostic result.

In any of the preceding embodiments, the feature of the sclera image can be a morphological feature and the database can comprise one or more sclera morphological features known to be associated with a healthy individual, a particular human population, and/or a disease or condition.

In any of the preceding embodiments, the device can further comprise a display member configured to connect to the imaging member and/or the processing member, wherein the display member is configured to display the subject's sclera image, one or more features of the sclera image, a health/disease status of the eye, a health/disease status of another organ or tissue of the subject, a physiological or pathological indicator of the subject, an overall health/ disease status of the subject, and/or a diagnostic or prognostic result.

In any of the preceding embodiments, the sclera of the subject can comprises one or more features, such as morphological features selected from the group consisting of a color feature, a blood vessel feature, and a surface morphology feature.

In any of the preceding embodiments, the device can further comprise an imaging member and a processing member, and the processing member can control the working status of the light source and/or the imaging member.

In any of the preceding embodiments, the device can comprise at least two, at least three, or at least four light sources, and the four light sources can be distributed to the left side, right side, upper side, and lower side of the positioning aperture, in order to facilitate exposure of the sclera for non-shadow and wide-field imaging when the eye turns to the left side, right side, upper side, and lower side, respectively.

In any of the preceding embodiments, the device can further comprise one or more signs for the light source in order to facilitate exposure of the sclera for non-shadow and wide-field imaging when the eye turns to view the one or more signs.

In any of the preceding embodiments, the light source can comprise a non-shadow bulb, a filament lamp, a mercury lamp, a LED (light-emitting diode), a laser-emitting device, or a combination thereof, and wherein the light source emits a polychromatic light, a monochromatic light, a narrowband light, or white light.

In any of the preceding embodiments, the positioning aperture can comprise an opening of a round, oval, ring, or eclipse shape, and comprises one or two openings for lifting or flipping the upper and/or the lower eyelid.

In any of the preceding embodiments, the device can further comprise one or more lenses and/or one or more sensor chips, wherein the one or more lenses transmit light from the eye onto the one or more sensor chips, and the one or more sensor chips receive and convert light on the surface to one or more images.

In any of the preceding embodiments, the device can further comprise one or more focusing member for adjusting the position of the one or more lenses, in order to form a good quality image of the sclera on the one or more sensor chips.

Also disclosed herein is a method of analyzing a sclera of a subject, comprising using the device of any of the preceding embodiments to obtain and analyze a non-shadow, wide-field image of the sclera.

In any of the preceding embodiments, the image of the sclera can be processed using an algorithm, the method comprising: (1) identifying an initial matched mask for a sclera image by identifying the cutoff threshold values of the S and V channels in the HSV space before finding the white area and black area's locations of a sclera image, using the software's corrosion operation, removing the black area to obtain a local sclera image which is smaller than the whole sclera, as the described initial mask; (2) treating a sclera image with gray-scale processing, for example, according to the gray-scale processing formula (I):

$$I = \min(255, (V + 100 \times fgb)) \times (\sim fv) \times ((1.5 - GB)^2 + 0.2) \quad (I),$$

wherein I is the final grey-scale image; V represents the image in the V channel of the HSV space, i.e., the grey-scale image under a normal condition; fv represents the extracted edge image after treating the V channel image with a discrete first-order difference; ~fv represents the opposite version of the image fv; and fgb represents the image after edge extracting on a GB image, and wherein the GB image is defined in formula (II):

$$GB = \frac{((G - 1.05 \times B) - \min(G - 1.05B))}{\max(G - 1.05 \times B)}, \quad (II)$$

wherein G and B represent the G channel and the B channel of a regular RGB color space, respectively, wherein in formula (I) and formula (II), fv ensures the final grey image's edge can stay at the right place within the sclera image area; $((1.5-GB)^2+0.2)$ can improve the difference or contrast between the sclera and the skin; and +100×fgb can remove the influence of the skin's white outer edge in order to increase the probability for the edge to stay at the right place; and (3) performing an energy bias correction using the initial mask obtained in the first step and the grey image obtained in the second step to calculate the curve's energy, for example, by using an eight-close-area method, wherein $I_{inside}$ and $I_{outside}$ are set as the average intensity of the inside and outside of the curve, respectively, and the energy of the curve is defined as E, which is calculated by using formula (III):

$$E = -\frac{1}{2}(I_{inside} - I_{outside})^2 \quad (III),$$

wherein the energy bias correction on the gray-scale image is calculated by formula (IV):

$$\Delta E = E_{energy} + \alpha \times E_{curve} + b \quad (IV),$$

wherein $E_{energy}$ refers to the energy of the initial mask's edge curve; $E_{curve}$ refers to the energy of the grey-scale image's edge curve after expanding the initial mask within the sclera area; α refers to the constant for the degree of mask edge's smoothness, and b refers to an empirical bias constant; wherein b can be adjusted in order to generate an outward pushing force to push the initial mask's edge to move outward quickly until when the edge reaches the original image's edge and ΔE=0, whereby the step serves the purpose of correcting the edge bias for the sclera image.

In any of the preceding embodiments, the analysis method can further comprise displaying a morphological feature of the sclera image and/or a diagnostic or prognostic result, wherein the morphological feature comprises a color feature, a vein feature, and/or a surface morphology feature of the sclera, and wherein the diagnostic or prognostic result comprises a disease/health condition of the eye, and/or a health state assessment of the subject.

In any of the preceding embodiments, the device or system can comprise one positioning aperture, and the left eye and the right eye engage the same positioning aperture one by one, for imaging the sclera of the left eye and the right eye, respectively.

BRIEF DESCRIPTION OF THE DRAWINGS

In order to more clearly illustrate the embodiments of the present disclosure, the drawings are briefly described below. It is apparent that the drawings in the following description are embodiments of the present disclosure, and other drawings may be obtained based on the present disclosure by a person with ordinary skill in the technical field without creative effort.

DETAILED DESCRIPTION

Figure 1:
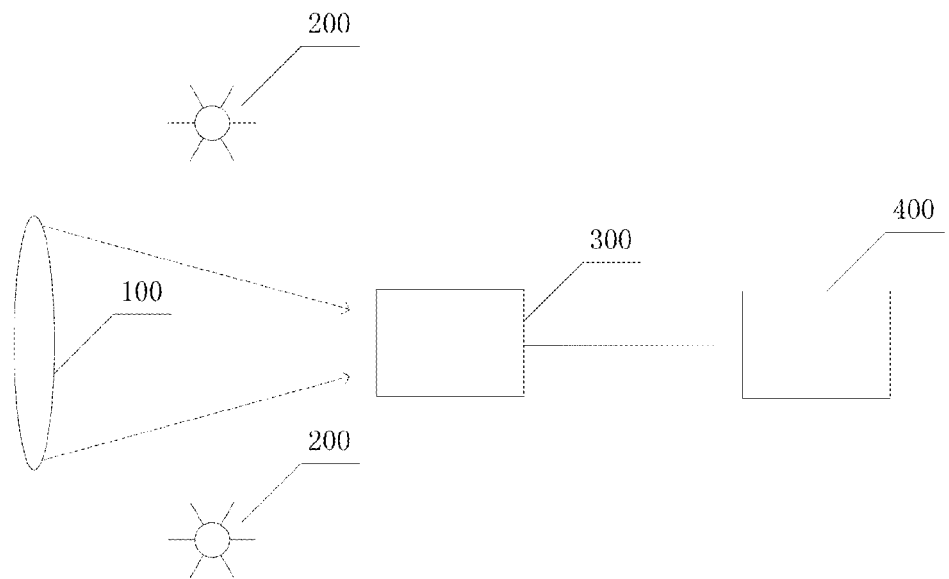
FIG. 1 is a schematic of an on-body device or system based on non-shadow imaging, according to one aspect of the present disclosure.

A detailed description of one or more embodiments of the claimed subject matter is provided below along with accompanying figures that illustrate the principles of the claimed subject matter. The claimed subject matter is described in connection with such embodiments, but is not limited to any particular embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure, or manner. Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described.

They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All publications referred to in this application are incorporated by reference in their entireties for all purposes to the same extent as if each individual publication were individually incorporated by reference.

All headings are for the convenience of the reader and should not be used to limit the meaning of the text that follows the heading, unless so specified.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6.

As used herein, the singular forms "a", "an", and "the" include plural references unless indicated otherwise. For example, "an" eye includes one or more eyes, and "a" method includes one or more methods.

It is understood that aspects and embodiments of the disclosure described herein include "consisting" and/or "consisting essentially of" aspects and embodiments.

Sclera Imaging Device and Method of Use

Eyes and especially fundi are imaged in order to detect different diseases or their symptoms. For example, in diabetes, damages may arise in fundi, which damages should be discovered as soon as possible. Devices used for this are called ophthalmoscopes or fundus cameras, and with those the inner parts of eye are examined by illuminating them through the pupil. Usually, when using a fundus camera, the person to be examined places her/his head into the examining device, and one or more trained person(s), such as a doctor, adjusts and moves manually the examining device and observes the object and, when necessary, launches manually the imaging device to take an image. Both eyes of the person to be examined are examined separately. This is a slow procedure and requires work contribution of a trained person.

Because the pupil of the eye contracts when light is directed thereto, the examinations are usually performed in a darkened room, and furthermore, eye drops can be used that enlarge the pupil and prevent it from contracting. Some patients, for example children, don't necessarily like applying of eye drops and recovering from the effect of them takes a long time. The patient and the nursing staff have to wait until the drops start to take effect before the examination can be performed. This slows down considerably the performing of the examination and also increases the threshold of the patient to go, for example, to routine examinations.

In patent publication WO 2010/051304, a device is disclosed which the user of the device, such as a doctor or an optician, can wear to the front of their own eyes to examine the eyes of the patient. The user of the device holds the device in front of the eye of the patient during the examination. The device emits infrared light and it is provided for turning the image prepared by the lens to correspond with the actual directions. The device described in the publication requires active participation of a trained person during the examination, and it is designed to operate only with infrared light.

In automated eye imaging one problem is that the devices become quite large and clumsy, when automatic focusing and similar properties are tried to be accommodated in the device. It would be a remarkable advantage if the size of the apparatus could be reduced such that even the person to be examined herself/himself could place the device in position and start the imaging. In practice, with the present technique even an automated device requires at least a trained assistant to use it.

In one aspect, by examining the anterior segment of an eyeball of a subject, people can not only understand the pathological changes of the eye, but also predict the physiological and/or pathological changes in the health/disease status of the subjects, including overall health status and health/disease status of other organs.

With current technologies, a slit lamp is usually used to observe the anterior segment of the eye to be measured. When imaging the sclera of the eye to be measured, a user of the art device needs to project the slit light of the slit lamp vertically to the eye of the subject in order to form a narrow optical section, and a sclera image within that narrow optical section is then obtained. By sweeping the slit light over the surface of the eye to be measured, the user can obtain multiple sclera images from multiple different optical sections. Finally, the sclera images of multiple optical sections are reconstructed together to form a whole image of the sclera, so that the user can obtain information about the pathological changes and/or the physiological and/or pathological health state of the subject by observing the sclera. The method of imaging the sclera by using the slit lamp needs to acquire multiple images of multiple sectional views in order to obtain the whole sclera image of the eye through image reconstruction. The method typically takes a long time to do the reconstruction and it is difficult to ensure seamless reconstruction of multiple images in order to restore the real condition of the sclera surface. In addition, if the slit lamp is used to image the entire sclera in a single image, then the slit light of the slit lamp needs to completely cover the eye to be measured, and a reflection image of the light source will be formed on the sclera, which undermines the sclera image to be taken.

In one aspect, the present disclosure provides an on-body analysis system and an analysis method for a human health status based on sclera imaging. In one aspect, the analysis device or system performs a wide-field imaging of the sclera with only one camera. In one aspect, the analysis device or system performs a non-shadow imaging of the sclera, e.g., the sclera image is free of any reflection of a light source. In one aspect, the analysis device or system performs imaging of all or a part of the sclera in a single image capturing (i.e., a one-time image capture), for example, using a single camera. In one aspect, the analysis system can perform a wide-field, non-shadow, one-time imaging with only one camera without moving camera position or the need of subsequent image reconstruction. In some embodiments, the process of forming a sclera image is short and the image quality is good, and the eye condition and the physiological condition of the human body (including the eye or another organ of the subject) can be analyzed according to the obtained sclera images.

In one aspect, provided herein is an on-body device or system, for example, for capturing an image of an eye of a subject and/or analysis of a health/disease condition of the subject. In one aspect, the on-body device or system is used for assessing a human health/disease state. In one aspect, the on-body device or system takes a non-shadow imaging of a sclera, or whites, of one or both eyes of a subject. In some embodiments, by analyzing the features (color, morphology, shape, pressure, etc.) of the sclera, physiological and/or pathological conditions of the subject can be assessed.

In one aspect, the device or system comprises a positioning aperture (such as a positioning hole) for positioning an eye to carry out an operation using the system. In some embodiments, the positioning aperture is for one eye, and the device or system comprises one or more positioning apertures. In other embodiments, the positioning aperture is for both eyes, and the device or system comprises one or more positioning apertures. The device can also comprise other features by which the desired position is achieved and the device is made to stay there during the imaging. Such may include, for example, different stickers, suction pads, vacuum pumps or similar, which can be part of the positioning aperture or be used together with the positioning aperture.

In any of the proceeding embodiments, the device or system can further comprise a support structure which surrounds the eye or eyes completely or partly, in addition to the positioning aperture. By means of the support structure, the device can be supported when it is in its place, and by means of it the device can be positioned to the measuring position or close to it such that the device's own adjustment can be reduced. By means of the support structure the device can also be hold in its place during the measuring. The support structure is placed against skin. The support structure is made preferably completely or partly of resilient material in order to make its placing and wearing against skin more comfortable for the object.

In any of the proceeding embodiments, the device or system can further comprise one or more light sources (e.g., an illuminating apparatus), which can be positioned on the opposite side of the positioning aperture from the eye to be tested. In one aspect, light emitting from the light source passes through the positioning aperture to obliquely illuminate the eye. In one aspect, oblique lighting uses a light source positioned at a low angle. In one aspect, due to the position of the light source relative to the positioning aperture, light emitting from the light source does not illuminate the eye through direct reflecting lighting. In any of the proceeding embodiments, the image of the light source itself can be formed on the eye's iris instead of on the sclera.

In any of the proceeding embodiments, the device or system can further comprise one or more imaging devices or apparatuses. In one aspect, the imaging apparatus captures an image of the eye, such as an image of the sclera of the eye. In one aspect, the imaging apparatus captures light from the eye (e.g., the sclera of the eye) due to the illumination of the eye by the light source. In one aspect, the image of the sclera is a wide-field image and/or a non-shadow image. In one aspect, the image of the sclera does not have a reflection of the light source.

In some aspects, the illumination arrangements can operate, for example, in visible light and infrared light areas. In some aspects, the different illumination arrangements of the device can operate in different wavelength regions. In some aspects, the illumination arrangements can be realized, for example, by LED (light-emitting diode) lighting fixtures, halogen technique, laser, bulbs or in some other way. In some aspects, the illumination arrangements can operate by being switched on for a predetermined time or by producing a flashlight type flash. In some aspects, if the illumination arrangement is able to be directed, it is moved by a motor. In some aspects, the illumination arrangement can include optics which can be adjustable, for example, for positioning of the light. In some aspects, the illumination arrangements are situated in respect of the imaging apparatus (such as a camera) in a way that they are separated from each other so that their optical axes do not meet.

In any of the proceeding embodiments, the device or system can further comprise one or more processing apparatuses. In one aspect, the processing apparatus is connected to the one or more imaging apparatuses.

In any of the proceeding embodiments, the imaging and/or processing apparatus can check the images. For example, the device can check if there are reflections in the image taken or in the image area, e.g., if there is light of the illumination arrangement reflected from the surface of the eye. If so, in one aspect, no data can be obtained from the image, and the image is useless either completely or partly. In one aspect, the device can perform this checking, for example, by means of the pattern recognition automatism when the reflections are clearly recognizable shapes in the image, or for example by studying the values of the pixels of the image or the values of the real-time image information obtained from the camera and by detecting the reflection included in the image, if the values of a pixel group exceed a given limit value. These can be done also directly from the camera sensor without actual imaging. The reflections are nearly always brighter than the aspired image data. When the device detects a reflection, it transmits the data to a control arrangement. Thereby, the control arrangement performs re-imaging of the spot in question and changes the parameters of the imaging such that there will be no reflection in the new image. The image or area including a reflection can also be ignored, if, for example the imaging area is compiled from a large number of separate images, and an individual image is small in comparison with the total image, or the reflection area is small in comparison with the complete image. Imaging or a part of the imaging is repeated, if there is a significant number of omitted images due to reflections or if they are situated such that there are significant apertures in the total image, i.e. points about which no information exists to be used. In addition to reflections, deviations can be looked for in the images, discovering of which may, for example, transfer the control arrangement to guide the imaging arrangement to take new images with new parameters. A new imaging can be performed, for example, in a greater resolution in the vicinity of the detected point or with a different imaging mode like by using a different wavelength camera or a different illumination or a camera of a more accurate imaging area. Absence of data can also be considered as a deviation. The device can also study whether there are reflections in the image area of the camera arrangement. For example, the situation is checked before the actual imaging. The device can also use camera arrangements or camera sensors which are provided for observing reflections before the actual imaging.

In one aspect, the processing apparatus saves/stores and/or processes image files. In another aspect, the processing apparatus extracts one or more characteristics of the eye from the captured image or images, such as a morphological feature of the sclera.

In any of the proceeding embodiments, the processing apparatus can compare the extracted feature of the sclera with one or more features in a database. For example, the morphological feature of the captured sclera image can be compared with the morphology of sclera images in a preset database. In any of the proceeding embodiments, the comparison can generate a report for the eye's health or disease conditions, the subject's health state, or a diagnostic result. In one aspect, the typical morphological characteristics, the corresponding diseases and/or pathological conditions are saved in the database in advance.

In any of the proceeding embodiments, the device or system can further comprise one or more display devices. In one aspect, the display device is connected to the one or more imaging apparatuses. In one aspect, the display device displays one or more images, one or more morphological characteristics of a sclera, one or more disease and/or health conditions (such as one or more disease and/or health conditions of an eye or a sclera, or of another organism), a subject's overall health state, and/or one or more assessment or diagnostic results.

In any of the proceeding embodiments, the one or more features or characteristics of a sclera comprise a color of all or part of the sclera, a feature of a blood vessel (such as a vein), and/or a feature of the sclera surface (such as the texture, a protrusion, an indentation, a lesion, a scar, etc.).

In one aspect, the processing apparatus controls the operation status of the light source, the imaging device, and/or the display device.

In any of the proceeding embodiments, the device or system can comprise about four light sources, such as four illuminating units. In one aspect, the four light sources are located on one side of the positioning aperture, opposite from the side where the eye is. In one aspect, the four light sources are located on a plane parallel to the plane on which the positioning aperture is located. In one aspect, the four light sources are located to the right, left, top, and bottom of the positioning aperture, for example, shown as light sources 200 in FIG. 2. In one aspect, the arrangement of the multiple light sources facilitates the imaging of the sclera, when the eyeball moves in any of the four directions. In one aspect, when the eyeball moves to the left, right, up, or down, the sclera is exposed to facilitate the imaging. In one aspect, the four light sources are on at the same time, and in other aspects, any one or more of the light sources are on while the others are off. In one aspect, any of the plurality of light sources can be used by itself to take a wide-field and non-shadow image of the sclera. In another aspect, at least two or three of the plurality of light sources can be used in combination, either simultaneously or sequentially in any suitable order, to take a wide-field and non-shadow image of the sclera. In any of the proceeding embodiments, the sclera image is taken using light from a region of or the entire sclera after the region or sclera is illuminated.

In any of the proceeding embodiments, the device or system can further comprise one or more signs in order to indicate view direction, or the direction in which a subject should move his or her eyeball during imaging. In one aspect, the sign is next to a light source. In another aspect, the sign is parallel to a light source. In one aspect, the sign is placed on a plane between the light source and the positioning aperture, and in particular embodiments, proximal to the light source. In one aspect, the illuminating apparatus comprises one or more signs beside the illuminating unit. In one aspect, each sign is on the proximal side of an illuminating unit compared to the positioning hole. In one aspect, the sign indicates a view direction for an eye to be tested, and/or the order in which the light sources should be viewed by the eye. In another aspect, the sign helps to direct the view in order to fully expose the sclera of the eye, for example, such that the base portion of the sclera can be exposed and imaged.

In one aspect, the light source comprises one or more non-shadow bulbs, one or more filament lamps, one or more low pressure mercury lamps, one or more LEDs, and/or one or more or laser-emitting devices or systems. In any of the preceding embodiments, the light from the light source(s) can be a polychromatic light or a monochromatic light.

In any of the preceding embodiments, the positioning aperture can be of any suitable shape, for example, a round, circle, oval, ring, rectangular, square, triangular, or irregular shape. In one aspect, the positioning aperture comprises two symmetrical eye positioning surfaces for a left eye and/or for a right eye of the subject. In another aspect, the positioning aperture comprises two symmetrical openings, for example, one on the upper side of an eye when the positioning aperture is positioned on the eye and the other one on the lower side of the eye. In some aspects, the openings are for lifting or flipping an eyelid, for example, using a finger or a tool.

In one aspect, the eye imaging device or system comprises one or more lenses and/or one or more sensor chips. In one aspect, the lens is used to transmit light to the surface of a sensor chip, in order to form an image. In another aspect, the sensor chip receives light on its surface in order to generate an image therefrom.

In one aspect, the eye imaging device or system comprises a focusing device, for example, connected to the lens. In one aspect, the focusing device is configured to connect to the lens, for example, upon the actuation of a motor. In any of the preceding embodiments, the focusing device adjusts the positioning of the lens so that an image of the sclera is generated on the sensor chip.

Also disclosed herein is a method of assessing a health and/or disease status of a subject, for example, a human, using the imaging device or system of any of the preceding embodiments or any suitable combination thereof. In one aspect, the method is an on-body method. In one aspect, the method comprises taking and/or analyzing a non-shadow image of a sclera, or whites, of one or both eyes of the subject. In another aspect, the method comprises identifying one or more features (e.g., a morphology characteristic) of the sclera of one or both eyes for analyzing a physiological and pathological condition of the subject. In one aspect, the method comprises positioning the imaging device or system on a subject in need thereof. In one aspect, the positioning aperture of the device or system is positioned on one or both eyes of the subject. For example, the two symmetrical eye positioning surfaces of the positioning aperture may be used to engage the left eye for taking a sclera image and then engage the right eye for taking another sclera image, or vice versa. In another aspect, the two symmetrical openings of the positioning aperture allow access of a finger or a tool to facilitate exposure of the sclera.

In any of the preceding embodiments, the method can further comprise starting the device or system such that the illuminating apparatus generates light, which can pass through the positioning hole to obliquely illuminate an eye of the subject. In one aspect, an image of the illuminating apparatus itself is formed on the iris of the eye instead of on the sclera. In another aspect, the subject observes the light source through the positioning aperture, and the light source illuminates the eye in the opposite direction of the subject's view direction (i.e., the direction in which the subject is looking at). In one aspect, the eye is illuminated and light is reflected from the eye to a sensor chip or surface. In another aspect, the method comprises using the imaging device to generate a non-shadow wide-field image of the sclera.

In any of the preceding embodiments, the method can further comprise saving and/or processing the image, for example, using a processing apparatus. In one aspect, the processing device extracts one or more features (e.g., morphological characteristics) from the one or more sclera images. In another aspect, the processing device compares the sclera image(s) to one or more images in a database. In another aspect, the processing device compares one or more parameters of the extracted feature to one or more references or models in the database. In a further embodiment, the method further comprises generating a report for a health and/or disease condition of the eye, the subject's health and/or disease status, one or more physiological indictors, one or more pathological indicators, and/or a diagnostic or prognostic result.

In any of the preceding embodiments, the extracted morphological characteristics of the sclera images can be pre-processed with a correction algorithm, such as an edge energy value correction algorithm, to ensure the integrity of the sclera area. In one aspect, the correction comprises the following steps. As a first step, the method comprises identifying an initial matched mask for a sclera image. For example, a cut-off threshold value of the S and/or V channels of the sclera image in the HSV space can be identified and used to process the sclera image, for example, to separate the image into segments or regions. In one aspect, the locations of the white area and black area of the eye in the HSV space can be identified. By using the software's corrosion operation, the black area can be removed from the sclera image. In one aspect, the method further comprises one or more erosion operations of the image in order to obtain a local sclera image which is smaller than the whole sclera. The local sclera image can be set as the initial mask.

In a second step, the method can comprise treating the sclera image with gray-scale processing, for example, according to the gray-scale processing formula (I):

$$I=\min(255,(V+100\times fgb))\times(\sim fv)\times((1.5-GB)^2+0.2) \quad (I),$$

wherein I is the final grey-scale image; V represents the image in the V channel of the HSV space, i.e., the grey-scale image under a normal condition; fv represents the extracted edge image after treating the V channel image with a discrete first-order difference; ~fv represents the opposite version of the image fv; and fgb represents the image after edge extracting on a GB image. In one aspect, the GB image is defined in formula (II):

$$GB = \frac{((G - 1.05 \times B) - \min(G - 1.05B))}{\max(G - 1.05 \times B)}, \quad (II)$$

wherein G and B represent the G channel and the B channel of a regular RGB color space, respectively.

In one aspect, in formula (I) and formula (II), fv ensures the final grey image's edge can stay at the right place within the sclera image area; $((1.5-GB)^2+0.2)$ can improve the difference or contrast between the sclera and the skin; and $+100\times fgb$ can remove the influence of the skin's white outer edge in order to increase the probability for the edge to stay at the right place.

In a third step, the method can comprise performing an energy bias correction. In one aspect, the initial mask obtained in the first step and the grey image obtained in the second step can be used to calculate the curve's energy, for example, by using an eight-close-area method. In one aspect, $I_{inside}$ and $I_{outside}$ are set as the average intensity of the inside and outside of the curve, respectively. In one aspect, the energy of the curve is defined as E, which is calculated by using formula (III):

$$E=-\frac{1}{2}(I_{inside}-I_{outside})^2 \quad (III).$$

In one other aspect, the energy bias correction on the gray-scale image is calculated by formula (IV):

$$\Delta E=E_{energy}+\alpha\times E_{curve}+b \quad (IV),$$

wherein $E_{energy}$ refers to the energy of the initial mask's edge curve; $E_{curve}$ refers to the energy of the grey-scale image's edge curve after expanding the initial mask within the sclera area; α refers to the constant for the degree of mask edge's smoothness, and b refers to an empirical bias constant. In one aspect, b can be adjusted in order to generate an outward pushing force to push the initial mask's edge to move outward quickly until when the edge reaches the original image's edge and ΔE=0. This step serves the purpose of correcting the edge bias for the sclera image.

In any of the preceding embodiments, the method can further comprise one or more of the following features: displaying one or more features (e.g., morphological characteristics) of a sclera image and/or one or more diagnostic or prognostic results, wherein the features of the sclera image comprise one or more of the following: a color of a region of the sclera, and a blood vessel characteristic (e.g., a feature of the veins) of the sclera surface. In one aspect, the diagnostic or prognostic results comprise the eye's disease or health condition, the subject's disease or health status, and/or a physiological and/or pathological information of the subject.

In one aspect, the present disclosure provides an on-body analysis system and methods for assessing a human health status based on non-shadow imaging of the sclera, or whites, of one or both eyes. In one aspect, the system comprises a positioning hole, an illuminating apparatus, and/or an imaging apparatus. In one aspect, when a device disclosed herein is used to generate an image of a sclera, the analysis system is first started to make the illumination light from the illumination device obliquely enter the eye to be measured through the positioning hole. In one aspect, the eye is illuminated by the light in the opposite direction of the view direction. In one aspect, the subject observes the illuminating apparatus through the positioning hole, and it is a feature of the system that the illuminating device illuminates the eye obliquely in the opposite direction of the direction in which the eye is looking. In one aspect, the image of the illuminating device is formed on the iris of the eye instead of on the sclera. In one aspect, the imaging apparatus is utilized to generate a sclera image, such as a non-shadow and wide-field image of all or part of the sclera of the eye. In another aspect, a processing apparatus is used for saving image files, extracting morphological characteristics from sclera images, comparing the images and/or parameters thereof to images and/or models in a database, and/or forming a report for the eye's disease condition, the subject's health status, a diagnostic and/or prognostic result, and/or physiological and/or pathological information.

In one aspect, the present disclosure provides wide-field, non-shadow imaging with only one camera without the need of taking, editing, and integrating multiple images. In one aspect, the present disclosure provides a device and method for imaging sclera without moving the camera position or image reconstruction. In one aspect, the presently disclosed method only takes a short time to obtain the image(s) of a sclera, for example, about one second, between about two and about ten seconds, between about ten and about 30 seconds, between about 30 seconds and one minute, between about one minute and about five minutes, or between about five minutes and about 10 minutes. In particular embodiments, the presently disclosed method takes less than five minutes to obtain the image(s) of a sclera. In one aspect, by using an illumination method in which light passes through a positioning hole to obliquely illuminate the testing eye, that the image of the illuminating apparatus itself is formed on the eye's iris instead of on the sclera. Thus, in one aspect, the reflection of the light source does not affect the image quality of the sclera. Since no reflection of the illuminating apparatus is generated on the sclera, the quality of sclera images can be improved. In a further embodiment, the system can utilize the sclera image(s) to obtain information of an eye disease or condition, and/or to predict a physiological and pathological change in the subject, and/or to assess the health status of the subject, and/or to generate a diagnostic or prognostic result. All those features of the present disclosure can provide helpful information for medical diagnosis and treatment.

In yet another aspect, disclosed herein are systems for monitoring eye health, that comprise: a scleral monitor comprising a) a wearable device comprising i) one or more positioning apertures, ii) one or more image sensors, iii) a CPU, iv) a memory storage device, v) one or more connecting wires, and vi) and a power source; and b) at least one preselected target region on or in the sclera, wherein the CPU receives images from the image sensors and then transmits the images to the memory storage device. Also disclosed are methods of using the disclosed systems to determine the health of an eye of an individual. In a further embodiment, disclosed herein are systems for monitoring eye health comprising a portable tablet device having a camera, and a lens assembly connectable to the camera of the portable tablet.

In some embodiments with reference to the drawings, disclosed herein is an on-body analysis device or system for assessing a human health status. In one aspect, the device or system takes one or more non-shadow images of a sclera, or whites of an eye, of one or both eyes. In one aspect, the device or system as shown in FIG. 1 is used to identify one or more features of the sclera for analyzing a physiological or pathological condition.

Referring to FIG. 1, an exemplary device or system comprises one or more positioning apertures 100 for positioning one or both eyes. In one aspect, light source 200 is located on the opposite side of the positioning aperture from an eye to be tested (not shown). In one aspect, the light passes through positioning aperture 100 to obliquely illuminate the eye, such that the image of light source 200 itself is formed on the eye's iris instead of on the sclera.

In one aspect, the device or system further comprises an imaging apparatus 300 for receiving light from the eye to be tested, after the eye is illuminated by light from the light source. In some embodiments, the device or system captures and/or processes light reflected from the oblique lighting, and generates non-shadow and wide-field image of the sclera of the eye.

In one aspect, the device or system further comprises a processing apparatus 400. In one embodiment, the processing apparatus or device is connected, via a permanent or releasable connection, to the imaging apparatus. In some aspects, the processing apparatus is configured to save or store image files, either locally or remotely. For example, the storage can be in another device connected to the processing apparatus via the internet or a local network, via a cable or wirelessly, e.g., through a Bluetooth connection. In some aspects, the processing apparatus is configured to extract one or more features (for example, morphological characteristics) from one or more sclera images. In some aspects, the processing apparatus is configured to compare the one or more features, or one or more parameters thereof, to one or more preset references or one or more models. The reference or model may be saved or retrievable locally from the processing device, or may be retrievable from another device connected to the processing apparatus via the internet or a local network, via a cable or wirelessly, e.g., through a Bluetooth connection. In some aspects, the processing apparatus is configured to generate a report for the eye's disease or health condition, the subject's overall health state, the health or disease condition of another organ, or a diagnostic or prognostic result. The report may comprise text, graph, light, sound, color, or any other suitable signal, or a combination thereof, and may be interactive with a user. In some embodiments, the device or system may comprise a display unit or terminal, or may be connected or connectable to a display unit or terminal, either using a cable or wirelessly, such as via a Bluetooth connection. In some embodiments, the display unit or terminal is a phone including mobile phones and cell phones, a computer including personal computers, laptops, tablets, or a signal emitting device, for example, for emitting a sound, light, vibration, or any combination thereof, as the signal for indicating the health or disease condition. In some embodiments, the display unit or terminal displays the report. In some embodiments, typical morphological characteristics of a sclera, including a normal or healthy sclera and the sclera of a subject known to have or have been diagnosed with a disease or condition, are saved in the database in advance. In some embodiments, also retrievable from the database is information of a health or disease status of one or more subjects, or information of physiological and pathological conditions, for example, from one or more human populations. The populations may be of different ethnical backgrounds or genetic backgrounds.

In one aspect, the illuminating apparatus 200 generates light, which can pass through positioning hole 100 to obliquely illuminate an eye on the other side of the positioning hole. Thus, the illuminating apparatus 200 itself forms a reflection on the eye's iris instead of on the sclera. In another aspect, the imaging apparatus 300 is utilized to generate one or more sclera images, and in some embodiments, light reflected from the sclera is used to generate non-shadow and wide-field images of the sclera. In another aspect, a processing apparatus 400 is used for saving image files, extracting one or more morphological characteristics from the sclera image, and/or comparing to models in a database. In one aspect, a report is generated for the eye's disease conditions, the subject's health status, a diagnostic result, and/or physiological and pathological information.

It can be seen from the above operation process of the analysis system that in one aspect, the system performs wide-field, non-shadow, one-time imaging with only one camera, and without moving camera position or image reconstruction. In one aspect, it only takes a short time to obtain the image or images. By using illuminating light that passes through a positioning hole to obliquely illuminate the eye, the image of the illuminating apparatus 200 itself is formed on the eye's iris instead of on the sclera, in order to reduce or eliminate the effect on the image quality of the sclera. In one aspect, the presently disclosed device and method do not generate reflection of the illuminating apparatus 200 on the sclera, thus improving the quality of sclera images. In another aspect, the device or system utilizes the sclera image or images to obtain information of one or more eye diseases and to predict a physiological or pathological change in the health status of a subject, or to predict a diagnostic or prognostic result, which can provide helpful information for medical diagnosis and prognosis.

In one embodiment, the relative position between the illumination apparatus 200 and the positioning hole 100 is adjustable if it is necessary to illuminate the subject's eye to be measured from different directions.

In one aspect, disclosed herein is an on-body device for analyzing a sclera of a subject, comprising: an on-body member comprising a positioning aperture for engaging an eye of a subject on one side of the positioning aperture, wherein the positioning aperture is on a plane and has a center; and a light source on the opposite side of the positioning aperture from the eye, wherein the line connecting the light source and the center of the positioning aperture intersects the plane at an angle of less than 90 degrees, wherein light from the light source, through the positioning aperture, obliquely illuminates the eye such that the reflection image of the light source is substantially outside of the sclera of the eye. In some embodiments, the angle is an oblique angle for illumination.

In any of the preceding embodiments, the angle can be less than about 85 degrees, about 80 degrees, about 75 degrees, about 70 degrees, about 65 degrees, about 60 degrees, about 55 degrees, or about 50 degrees. The angle can also be of any degree between the above-mentioned angles, such as between about 55 degrees and about 50 degrees.

In any of the preceding embodiments, the angle can be less than about 45 degrees, about 40 degrees, about 35 degrees, about 30 degrees, about 25 degrees, about 20 degrees, about 15 degrees, about 10 degrees, or about 5 degrees. The angle can also be of any degree between the above-mentioned angles, such as between about 25 degrees and about 30 degrees.

In any of the preceding embodiments, all or part of the reflection image of the light source can be on the iris of the eye, for example, at least about 50%, about 60%, about 70%, about 80%, about 90%, about 95%, or about 99% of the area of the reflection image is on the iris of the eye. In any of the preceding embodiments, less than about 50%, about 40%, about 30%, about 20%, about 10%, about 5%, or about 1% of the area of the reflection image can be on the sclera of the eye.

When the reflection image of the light source is substantially outside of the sclera of the eye, it can include that at least about 50%, about 60%, about 70%, about 80%, about 90%, about 95%, or about 99% of the area of the reflection image is outside of the sclera of the eye.

Figure 2:
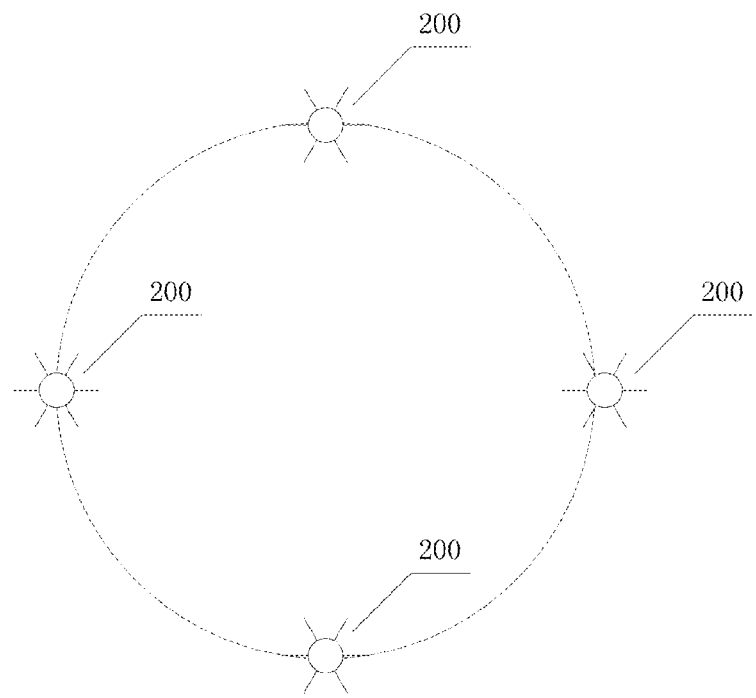
FIG. 2 shows an exemplary layout of the illuminating units, according to one aspect of the present disclosure.

In other embodiments, the illumination device 200 and the positioning hole 100 are fixed relatively to each other. In one aspect, by using a set of multiple illumination devices 200, illumination and imaging in different directions of the subject's eyes can be performed. As shown in the example of FIG. 2, the illuminating apparatus 200 comprises four illuminating units, which are located to the right, left, up, and down of the positioning hole 100, in order to facilitate obtaining four-directional, non-shadow, and wide-field images of the sclera when the eyeball moves in those four directions. In one aspect, the image of the sclera is taken using an illuminating light in the opposite direction of the eyeball's view direction. In any of the preceding embodiments, one or any suitable number of light sources can be placed at any suitable position for the subject's eyeball to view, as long as the eye's viewing the light source (and/or a sign indicating the light source) facilitates the exposure of the sclera and/or avoids formation of a reflective image of the light source on the sclera.

In one embodiment, an extracted feature (such as a morphological characteristic) of a sclera image is pretreated with a correction algorithm, such as an edge energy value correction algorithm, to ensure the integrity of the sclera area.

In one aspect, the method comprises identifying an initial matched mask for a sclera image. For example, a cut-off threshold value of the S and/or V channels of the sclera image in the HSV space can be identified and used to process the sclera image, for example, to separate the image into segments or regions. In one aspect, the locations of the white area and black area of the eye in the HSV space can be identified. By using the software's corrosion operation, the black area can be removed from the sclera image. In one aspect, the method further comprises one or more erosion operations of the image in order to obtain a local sclera image which is smaller than the whole sclera. The local sclera image can be set as the initial mask.

In any of the preceding embodiments, the method can further comprise treating the sclera image with gray-scale processing, for example, according to the gray-scale processing formula (I):

$$I=\min(255,(V+100 \times fgb)) \times (\sim fv) \times ((1.5-GB)^2+0.2) \quad (I),$$

wherein I is the final grey-scale image; V represents the image in the V channel of the HSV space, i.e., the grey-scale image under a normal condition; fv represents the extracted edge image after treating the V channel image with a discrete first-order difference; ~fv represents the opposite version of the image fv; and fgb represents the image after edge extracting on a GB image. In one aspect, the GB image is defined in formula (II):

$$GB = \frac{((G - 1.05 \times B) - \min(G - 1.05B))}{\max(G - 1.05 \times B)}, \quad (II)$$

wherein G and B represent the G channel and the B channel of a regular RGB color space, respectively.

In one aspect, in formula (I) and formula (II), fv ensures the final grey image's edge can stay at the right place within the sclera image area; $((1.5-GB)^2+0.2)$ can improve the difference or contrast between the sclera and the skin; and +100×fgb can remove the influence of the skin's white outer edge in order to increase the probability for the edge to stay at the right place.

In any of the preceding embodiments, the method can further comprise performing an energy bias correction. In one aspect, the initial mask obtained in the first step and the grey image obtained in the second step can be used to calculate the curve's energy, for example, by using an eight-close-area method. In one aspect, $I_{inside}$ and $I_{outside}$ are set as the average intensity of the inside and outside of the curve, respectively. In one aspect, the energy of the curve is defined as E, which is calculated by using formula (III):

$$E = -\tfrac{1}{2}(I_{inside} - I_{outside})^2 \tag{III}$$

In one other aspect, the energy bias correction on the gray-scale image is calculated by formula (IV):

$$\Delta E = E_{energy} + \alpha \times E_{curve} + b \tag{IV}$$

wherein $E_{energy}$ refers to the energy of the initial mask's edge curve; $E_{curve}$ refers to the energy of the grey-scale image's edge curve after expanding the initial mask within the sclera area; α refers to the constant for the degree of mask edge's smoothness, and b refers to an empirical bias constant. In one aspect, b can be adjusted in order to generate an outward pushing force to push the initial mask's edge to move outward quickly until when the edge reaches the original image's edge and $\Delta E=0$. This step serves the purpose of correcting the edge bias for the sclera image.

In any of the preceding embodiments, the analysis device or system can further comprise a display, which can be a device or system, and which can be connected to the imaging apparatus via a cable, another device, or wirelessly for example via a Bluetooth connection. In one aspect, the display displays one or more images, one or more features (such as morphological characteristics) of the sclera, a disease or health condition of the eye, a disease or health condition of another organ or tissue of the subject, the subject's overall health status, one or more test results, one or more diagnostic results, one or more prognostic results, and/or physiological and pathological information. In any of the preceding embodiments, the display can comprise a display screen, a signal light, a device capable of emitting an audible signal, or any suitable combination thereof.

In any of the preceding embodiments, the processing apparatus 400 can comprise a computer, a tablet, a cell phone, a microprocessor, or any suitable combination thereof. In one embodiment, the processing apparatus 400 is a microprocessor. Any suitable processing device 400 may be used as long as the functions of saving and/or processing the sclera images can be achieved.

In any of the preceding embodiments, the processing apparatus 400 can also be used to supply power to the illuminating device 200. In other embodiments, the illuminating device 200 is powered by the utility power through a plug. Any suitable power supply mode for the illuminating device 200, the imaging device 300, the processing device 400, and/or the display may be used.

In any of the preceding embodiments, the device can comprise a power supply for operating the different parts of the device. This may be an accumulator or a battery or a connection to an external power supply, or similar. The device can also be provided to be charged by placing it in a dock charger or to charge it by wireless means. In any of the preceding embodiments, the device can comprise a switch, the switching of which causes initialization of the functions of the device and moving to the operation mode. The device may also comprise some other arrangement, by which it is moved to the operation mode. In the operation mode, the device can check whether it is in its position in the front of the eyes. This may have been realized, for example, by different detectors. The part of the device to be placed in the front of the eyes may comprise an electronic or mechanical detector to detect whether it is pressed against the skin. This can also be realized by identifying reflection properties of an eye or eyes. In detecting the distance, also an image analyzing program can be used, where, for example, the size of the eye is recognized or the camera arrangement is focused as a default for a predetermined distance, and when the image is sharp, the imaging area of the camera arrangement or the operating area of its own focusing motor is reached. The device can also be started manually to perform the imaging when it is placed in its position. This can be done by the supervisor or object of the imaging when he/she feels that the device is placed in its position. The device is provided also for switching itself off or for shifting to a standby mode when the imaging was performed acceptably. The device can further be realized such that it is placed in a dock charger or similar arrangement and it starts when it is removed from the dock charger and switches off when it is returned to the dock charger.

In any of the preceding embodiments, the illuminating device 200, the imaging device 300, the processing device 400, and/or the display may be structurally integrated in one device or system. In any of the preceding embodiments, the processing apparatus 400 and the display can be integrated in a computer or processor. In other embodiments, the display device and the processing device 400 are separate from each other.

In any of the preceding embodiments, the one or more features of the sclera can comprise one or more morphological characteristics of the sclera, such as characteristics of a color, a vein and/or a surface of the sclera.

In any of the preceding embodiments, the processing apparatus 400 can compare the sclera image to the one or more features of the sclera, health/disease status, or physiological or pathological information in a database. In one aspect, if a feature of the sclera image or a parameter thereof fits the sclera feature associated with a health/disease status or physiological or pathological information in the database, the system can output the health/disease status or physiological or pathological information as a result, for example, for diagnosis, guiding a treatment decision, and/or for prognosis. In some embodiments, if a sclera image fits multiple sclera features in the database, the processing apparatus 400 can output health status and physiological and pathological information which correspond to at least one or all of the multiple sclera features. In one aspect, the multiple sclera features are integrated into one report that is the output of the device or system.

In any of the preceding embodiments, the sclera surface morphological features can include but are not limited to a spot, a dot, a protrusion, an indentation, a groove, a band, a post, a bubble, fogging, redness or other change in color, or a combination thereof. The sources of the sclera morphological features can come from, but are not limited to, literature, papers, reports or medical records of one or more subjects or a population of normal subjects and/or patients of various conditions and diseases.

In any of the preceding embodiments, the diagnostic or prognostic result can comprise the prediction of the eye's health/disease condition, the subject's overall health/disease status or status with regarding to a particular organ or tissue, physiological and pathological information, and/or a diagnostic result.

In any of the preceding embodiments, the processing apparatus 400 can save image files taken by the imaging apparatus 300, extract a morphological characteristic from the sclera image, compare the characteristic to a model in a database, and generate a prediction report for the eye's disease/health condition, the subject's overall health/disease status or status with regarding to a particular organ or tissue, physiological and pathological information, and/or a diagnostic result.

In one other aspect, provided herein is a method for forming the preset database, comprising: inputting a sclera image from a book, a published literature, a report, and/or a medical record, of one or more subjects or a population of normal subjects and/or patients of various conditions and diseases; extracting and inputting the sclera characteristics, for example, in colors, vein and surface morphology from the sclera images; saving the extracted sclera characteristics and their corresponding eye disease conditions, health status, physiological and pathological information or diagnostic results so that a database is formed. The database can be saved locally in the processing device or in another device that is accessible via a cable, via the internet, or wirelessly such as via a Bluetooth connection.

In one aspect, the device or method provided herein uses the processing device 400 to control the operating status of the illuminating device 200 and/or the imaging device 300.

In any of the preceding embodiments, the operating state of the illuminating device 200 includes, but is not limited to, a switch, of the illuminating device 200, illumination brightness or the intensity of the light from the illuminating device 200, and illumination time of the illuminating device 200.

In any of the preceding embodiments, the processing device 400 can be used to control the imaging device 300 to automatically image the sclera. In other embodiments, the imaging device 300 may also be manually controlled, for example, by a user, who may be a medical professional or the subject whose eye is being tested. The present disclosure does not limit the way in which the imaging device 300 is controlled, which may be adjusted according to the situation.

In any of the preceding embodiments, the processing device 400 can be used to control the operating states of the illuminating device 200 and the imaging device 300. In one embodiment, the processing device 400 controls the operation time of the illuminating apparatus 200, and within this illumination time, the processing device 400 also controls the imaging apparatus 300 to generate one or more images of the sclera. This way, the device or system can achieve automatic imaging of the sclera.

In any of the preceding embodiments, the processing device 400 can be used to control the operating states of the illuminating device 200. In one embodiment, the processing device 400 controls the operation time of the illuminating apparatus 200, while within the illumination time, a user (e.g., a medical professional or the subject whose eye is being tested) can control the imaging apparatus 300 to generate one or more images of the sclera. In one embodiment, the processing device 400 only needs to control the operation state of the illuminating device 200, thereby reducing the processing load of the processing device and enhancing the work stability of the device or system.

In any of the preceding embodiments, the processing device 400 can be used to control the operating states of the imaging apparatus 300. In one aspect, the processing device 400 controls the imaging device 300 to automatically image the sclera. In one embodiment, the processing device 400 only needs to control the operation state of the imaging device 300, thereby reducing the processing load of the processing device 400, and enhancing the work stability of the analysis device or system.

In any of the preceding embodiments, the processing device 400 can comprise one or more processing units. For example, the processing device 400 can comprise a first and a second processing unit. In one aspect, the first processing unit extracts one or more features (such as morphological features) of the saved sclera image or images and compares with the sclera features in a preset database, for example, for generating diagnostic results including eye disease information, health status and physiological and pathological information. In one aspect, the preset database is stored in the first processing unit, and the second processing unit is for controlling one or more operation states of the illuminating device 200 and/or the imaging device 300. In one embodiment, the first processing unit and the second processing unit are integrated in one device. In some embodiments, the first and second processing units are not structurally integrated. In other embodiments, the functions of the first and second processing units are implemented by two separate units or means.

In any of the preceding embodiments, the illuminating device 200 can comprise one or more lighting units arranged around an axis that is perpendicular to the plane of the positioning hole. In particular embodiments, the one or more lighting units can perform oblique illumination with different angles and azimuths to the positioning holes as required.

It should be noted that the present disclosure is not limited to the specific position of the illuminating unit as long as the light of the illuminating unit can obliquely pass through the positioning hole 100 so that the eye to be tested is completely illuminated without shadow. The present disclosure is not limited to the specific number and/or position of the illuminating units.

In any of the preceding embodiments, the relative positions of the illuminating units and the positioning hole 100 can be adjustable, such that when the morphological condition of the sclera or eye is special, a user can adjust the relative positions to ensure the illuminating unit's image is formed on the iris and not on the sclera. In other embodiments, the relative position of the illuminating unit to the positioning hole 100 is fixed, which reduces the complexity of operation of the analysis system and facilitates the use by a user who has not used the device before.

In any of the preceding embodiments, the pattern in which the illuminating units are distributed can be adjusted as long as the light of the illuminating unit can obliquely pass through the positioning hole 100.

In one embodiment, an exemplary distribution of illuminating apparatus 200 is shown in FIG. 2. In one aspect, the illuminating apparatus 200 comprises four illuminating units, which are arranged at the end points where a first and a second diameter of a preset circle intersect with the circle. In one aspect, the plane of the circle is parallel to the plane of the positioning aperture 100. In another embodiment, four illuminating units are located right, left, up, and down to the positioning hole, in order to facilitate obtaining four-directional, non-shadow, and wide-field images of the sclera when the eyeball moves and views in those four directions.

In any of the preceding embodiments, the first diameter can be a diameter in the horizontal direction of the preset circle when the analysis system is set. In other embodiments, the first diameter is a diameter in any direction of the preset circle. In any of the preceding embodiments, the second diameter may be perpendicular to the first diameter.

In any of the preceding embodiments, the processing apparatus 400 can control the operation state of the illuminating apparatus 200 to turn on the illuminating units in any suitable order to illuminate the eye to be measured. The patient to be measured looks toward the illuminating unit (or a sign indicating the illuminating unit) when the unit is turned on. In one aspect, the processing device 400 controls the imaging device 300 to image the sclera of an eye to be measured during each illuminating unit's operation period, for example, by automatic imaging or manual imaging.

In any of the preceding embodiments, the illuminating system can further comprise one or more indication signs associated with each illuminating unit. In one aspect, the indication sign is arranged on the side of an illumination unit near the positioning hole to indicate the observing position and observation order for the eye to be tested and to help fully expose the sclera. In another aspect, the indication sign comprises a Roman numeral, so that the patient to be examined can recognize the order for looking to the illuminating units. In other embodiments, the indication sign comprises one or more Chinese characters, symbols, or Roman numerals, or any combination thereof.

In any of the preceding embodiments, the illuminating unit can comprise a non-shadow lamp, an incandescent lamp, a low-pressure mercury lamp, an LED lamp, a laser, or any combination thereof. In any of the preceding embodiments, the illumination light emitted by the illuminating unit can be a compound light or monochromatic light. In any of the preceding embodiments, the illumination light emitted by the illuminating unit can be a narrow-band light or white light.

In any of the preceding embodiments, the illuminating units can satisfy the requirement that the wavelength of the illumination light covers the visible light region and/or that the color temperature meets the authenticity and/or comfort requirements of the eye to be measured. In any of the preceding embodiments, the wavelength of the illumination light can be adjusted according to the specific needs of a user or a particular test.

In any of the preceding embodiments, the positioning hole 100 can be a circular hole, an elliptical hole, or an annular hole. The present disclosure is not limited to the specific shape of the positioning hole 100, and in some aspects, the shape of the positioning aperture can be adjusted according to the specific needs of a user or a particular test.

Figure 3:
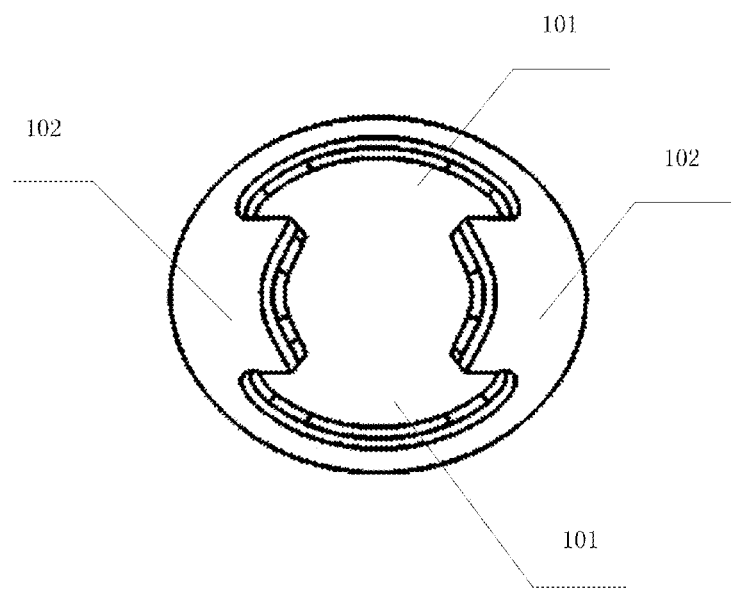
FIG. 3 shows an exemplary structure of a positioning aperture (such as a positioning hole), according to one aspect of the present disclosure.

In a specific embodiment as shown in FIG. 3, the positioning hole 100 comprises two bilateral symmetric positioning surfaces 102 located on both side walls of the positioning hole 100 and two upper and lower symmetric finger holes 101 for opening and closing an eyelid. In one aspect, the virtual line connecting the centers of both finger holes 101 passes through a diameter of the positioning hole 100. In one embodiment, the finger holes 101 serve to facilitate the finger to lift or turned over the eyelid, thereby exposing the sclera to be examined sufficiently. The present disclosure is not limited to the specific structure of the positioning hole, which in some aspects, may be adjusted according to the specific needs of a user or a particular test.

In any of the preceding embodiments, the imaging device 300 can comprise one or more lenses and/or one or more sensor chips. In one aspect, the lens is used to transmit light onto the described sensor chip. In one aspect, the sensor chip is used to receive light on its surface and generate an image of the sclera. In any of the preceding embodiments, the lens can comprise a lens sheet and/or other imaging elements. In some embodiments, the lens comprises a lens group of the same or different lenses. The present disclosure is not limited to the specific form, number, or arrangement of the lens, as long as the light can be imaged onto the sensor chip. In some aspects, the lens or lens group may be adjusted according to the specific needs of a user or a particular test.

In any of the preceding embodiments, the sensor chip can be, but not limited to, a charge-coupled sensing chip, or a complementary metal oxide semiconductor sensing chip. The present disclosure is not limited to the specific form, number, or arrangement of the sensor chip, and in some aspects, the sensor chip or set of sensor chips may be adjusted according to the specific needs of a user or a particular test.

In any of the preceding embodiments, the analysis system can further comprise one or more focusing devices. In one aspect, the focusing device is connected to the lens for adjusting the lens to image the sclera on the sensor chip, so as to ensure the sharpness of the sclera image. In one embodiment, the focusing apparatus is a manual focusing device, and the sclera image is focused on the sensor chip by a manual adjustment. However, the present disclosure does not limit the focusing means of the focusing device, which in some aspects, may be adjusted according to the specific needs of a user or a particular test. In one embodiment, the focusing device is an auto-focusing device. In another embodiment, the auto-focus device is controlled by the processing device 400 to realize an auto-focusing function.

In one aspect, the auto-focusing device performs an auto-focusing function by an ultrasonic motor. The principles and apparatus configuration for realizing the auto-focusing are well known to those skilled in the technical field. The present disclosure does not limit the means in which the auto-focusing device performs auto-focusing and the structure of the specific device in some aspects may be adjusted according to the specific needs of a user or a particular test.

Figure 4:
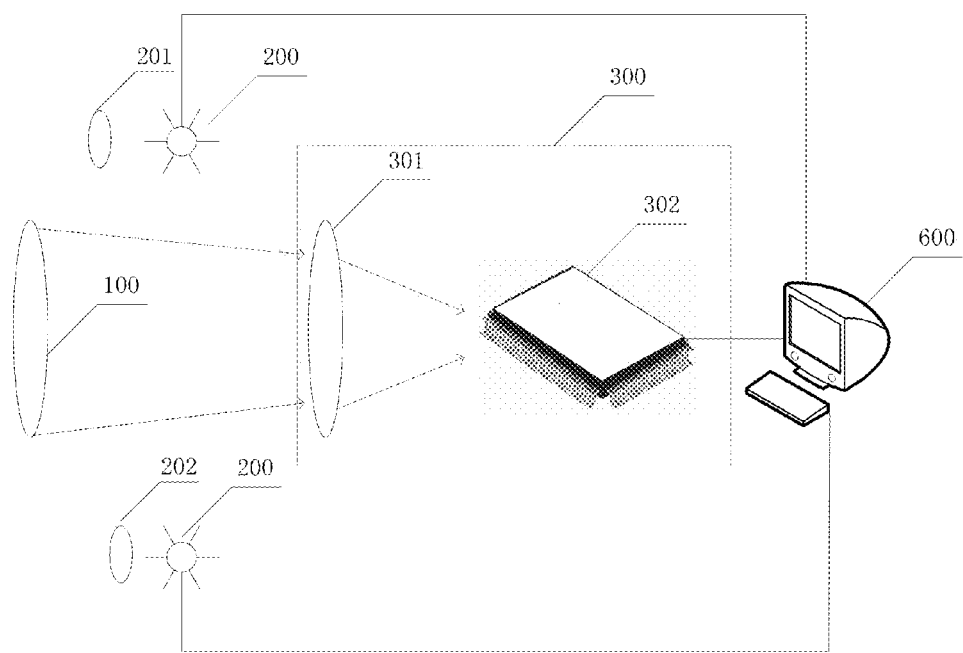
FIG. 4 shows an exemplary structure of an on-body device or system based on non-shadow imaging, according to one aspect of the present disclosure.

In any of the preceding embodiments, the analysis system based on non-shadow imaging of the sclera can comprise the components as shown in FIG. 4. In one aspect, numbers 201 and 202 represent the indication signs, 600 represents a computer that integrates the processing apparatus 400 and the display apparatus, 301 represents the lens, and 302 represents the sensor chip.

In one aspect, provided herein is an on-body analysis system and methods for assessing human health status based on non-shadow imaging of sclera, or whites, of one or both eyes. In one aspect, the system comprises a positioning hole 100, illuminating apparatus 200, and/or an imaging apparatus 300. When a described analysis system is forming images of a sclera, the analysis system is first started to make the illumination light of the illumination device 200 obliquely enter the eye to be measured through the positioning hole 100, and then the eye is illuminated by the back light (light reflected from the eye). In one aspect, the subject observes the indication signs 201 and 202 of the illuminating apparatus through the positioning hole 100, thus the illuminating device 200 illuminates the eye obliquely in the opposite direction (back light) of the direction in which the eye is looking, so that the image of the illuminating device 200 is formed on the iris of the eye. In one aspect, the imaging apparatus 300 is utilized to generate a sclera image, which is a non-shadow and wide-field images of the eye's sclera. In another aspect, a processing apparatus 600 is used for saving image files, extracting morphological characteristics from sclera images, comparing to the models in the database, and/or forming a report for the eye's disease conditions, a subject's health status, and/or a diagnostic result of physiological and/or pathological information.

In one aspect, the system performs wide-field and non-shadow and one-time imaging with only one camera without moving camera position or image reconstruction. In one aspect, it only takes a short time to obtain the images. In one aspect, the illuminating method uses light passing through a positioning hole obliquely to illuminate the testing eye, such that the image of the illuminating apparatus 200 itself is formed on the eye's iris instead of on the sclera. Image of the light source on the sclera affects the image quality of the sclera and should be avoided or reduced. In one aspect, the device or method herein does not generate reflection of the illuminating apparatus 200 on the sclera, which improves the quality of sclera imaging. In a further aspect, the system utilizes the sclera images to obtain information of eye diseases and to predict the physiological and pathological changes in the health status of subject or diagnostic results, which can provide helpful information for medical diagnosis.

Figure 5:
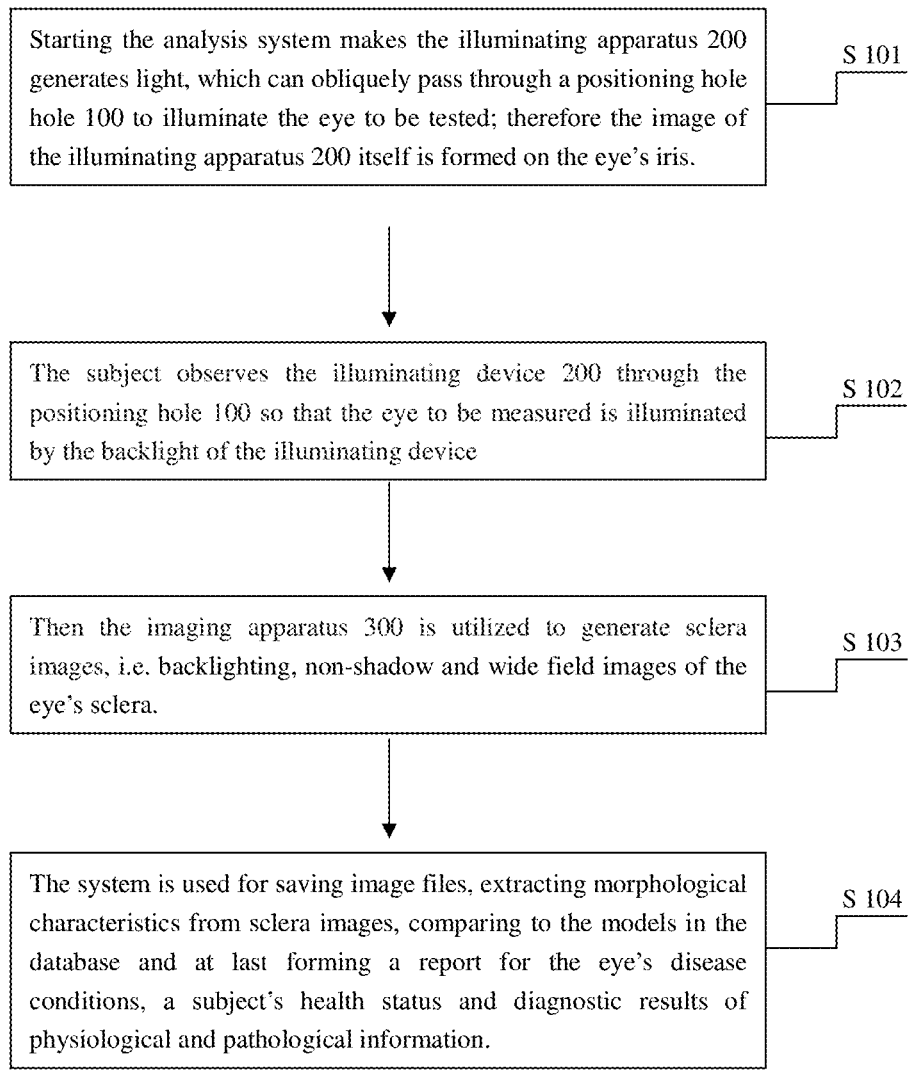
FIG. 5 shows an exemplary method for assessing a human health or disease status based on a non-shadow image of a sclera of the human subject, according to one aspect of the present disclosure.

In one aspect, provided herein is an on-body analysis device or system, and a method of use, for assessing a human health state, for generating a wide-field, non-reflection image of a sclera of an eye. In any of the preceding embodiments, the method can utilize the sclera image's characteristics to perform physiological and pathological analysis of human health status, for example, as shown in FIG. 5. In one aspect, the method comprises steps S101-S104.

In one aspect, S101 comprises starting the analysis system such that the illuminating apparatus 200 generates light, which obliquely passes through a positioning hole 100 to illuminate the eye to be tested. In one aspect, the image of the illuminating apparatus 200 itself is formed on the eye's iris and not on the sclera.

In one aspect, S102 comprises having a subject observe the illuminating device 200 through the positioning hole 100 so that the eye to be measured is illuminated by the reflected light of the illuminating device via the sclera.

In one aspect, S103 comprises using the imaging apparatus 300 to generate a sclera image, which is a non-shadow and wide-field image of the eye's sclera.

In one aspect, S104 comprises saving image files, extracting morphological characteristics from sclera images, comparing the extracted characteristics to the models in the database, and/or forming a report for the eye's disease conditions, a subject's health status, a diagnostic results, and/or physiological and pathological information.

The present inventors found that by using light passing through a positioning hole to obliquely illuminate the testing eye, the image of the illuminating apparatus itself is formed on the eye's iris instead of on the sclera. Thus, the image quality of the sclera is not affected. In one aspect, the method disclosed herein does not generate reflection of the illuminating apparatus 200 on the sclera, thus improving the quality of the sclera images. In another aspect, the system utilizes the sclera images to obtain information of an eye disease and/or to predict a physiological and/or pathological change in the health status of subject or a diagnostic or prognostic result, which can provide helpful information for medical diagnosis and/or prognosis.

In any of the preceding embodiments, the analysis method can further comprise displaying a sclera image and its characteristics, which in some aspects comprise characteristics in colors, vein, and/or surface morphology from sclera images.

In any of the preceding embodiments, the extracted morphological characteristics of sclera images can be pretreated with a correction algorithm, such as an edge energy value correction algorithm, for example, to ensure the integrity of the imaged sclera area. In one aspect, the method comprises identifying an initial matched mask for a sclera image. For example, a cut-off threshold value of the S and/or V channels of the sclera image in the HSV space can be identified and used to process the sclera image, for example, to separate the image into segments or regions. In one aspect, the locations of the white area and black area of the eye in the HSV space can be identified. By using the software's corrosion operation, the black area can be removed from the sclera image. In one aspect, the method further comprises one or more erosion operations of the image in order to obtain a local sclera image which is smaller than the whole sclera. The local sclera image can be set as the initial mask.

In any of the preceding embodiments, the method can further comprise treating the sclera image with gray-scale processing, for example, according to the gray-scale processing formula (I):

$$I=\min(255,(V+100 \times fgb)) \times (\sim fv) \times ((1.5-GB)^2+0.2) \quad (I),$$

wherein I is the final grey-scale image; V represents the image in the V channel of the HSV space, i.e., the grey-scale image under a normal condition; fv represents the extracted edge image after treating the V channel image with a discrete first-order difference; ~fv represents the opposite version of the image fv; and fgb represents the image after edge extracting on a GB image. In one aspect, the GB image is defined in formula (II):

$$GB = \frac{((G - 1.05 \times B) - \min(G - 1.05B))}{\max(G - 1.05 \times B)}, \quad (II)$$

wherein G and B represent the G channel and the B channel of a regular RGB color space, respectively.

In one aspect, in formula (I) and formula (II), fv ensures the final grey image's edge can stay at the right place within the sclera image area; $((1.5-GB)^2+0.2)$ can improve the difference or contrast between the sclera and the skin; and +100×fgb can remove the influence of the skin's white outer edge in order to increase the probability for the edge to stay at the right place.

In any of the preceding embodiments, the method can further comprise performing an energy bias correction. In one aspect, the initial mask obtained in the first step and the grey image obtained in the second step can be used to calculate the curve's energy, for example, by using an eight-close-area method. In one aspect, $I_{inside}$ and $I_{outside}$ are set as the average intensity of the inside and outside of the curve, respectively. In one aspect, the energy of the curve is defined as E, which is calculated by using formula (III):

$$E=-\tfrac{1}{2}(I_{inside}-I_{outside})^2 \quad (III).$$

In one other aspect, the energy bias correction on the gray-scale image is calculated by formula (IV):

$$\Delta E = E_{energy} + \alpha \times E_{curve} + b \quad (IV),$$

wherein $E_{energy}$ refers to the energy of the initial mask's edge curve; $E_{curve}$ refers to the energy of the grey-scale image's edge curve after expanding the initial mask within the sclera area; α refers to the constant for the degree of mask edge's smoothness, and b refers to an empirical bias constant. In one aspect, b can be adjusted in order to generate an outward pushing force to push the initial mask's edge to move outward quickly until when the edge reaches the original image's edge and ΔE=0. This step serves the purpose of correcting the edge bias for the sclera image.

In any of the preceding embodiments, the method can further comprise displaying the sclera images, the images' morphological features, and/or the diagnostic or prognostic results.

In any of the preceding embodiments, the image morphological features can comprise color features, blood vein characteristics, and/or surface morphological features of the sclera. In any of the preceding embodiments, the diagnostic or prognostic results can comprise eye disease information and a subject's health of status of the physiological and pathological information.

In any of the preceding embodiments, the saved sclera images may be displayed by a display device or saved in a processing device, and may be subjected to operations such as feature extraction and/or analysis and comparison.

Figure 6:
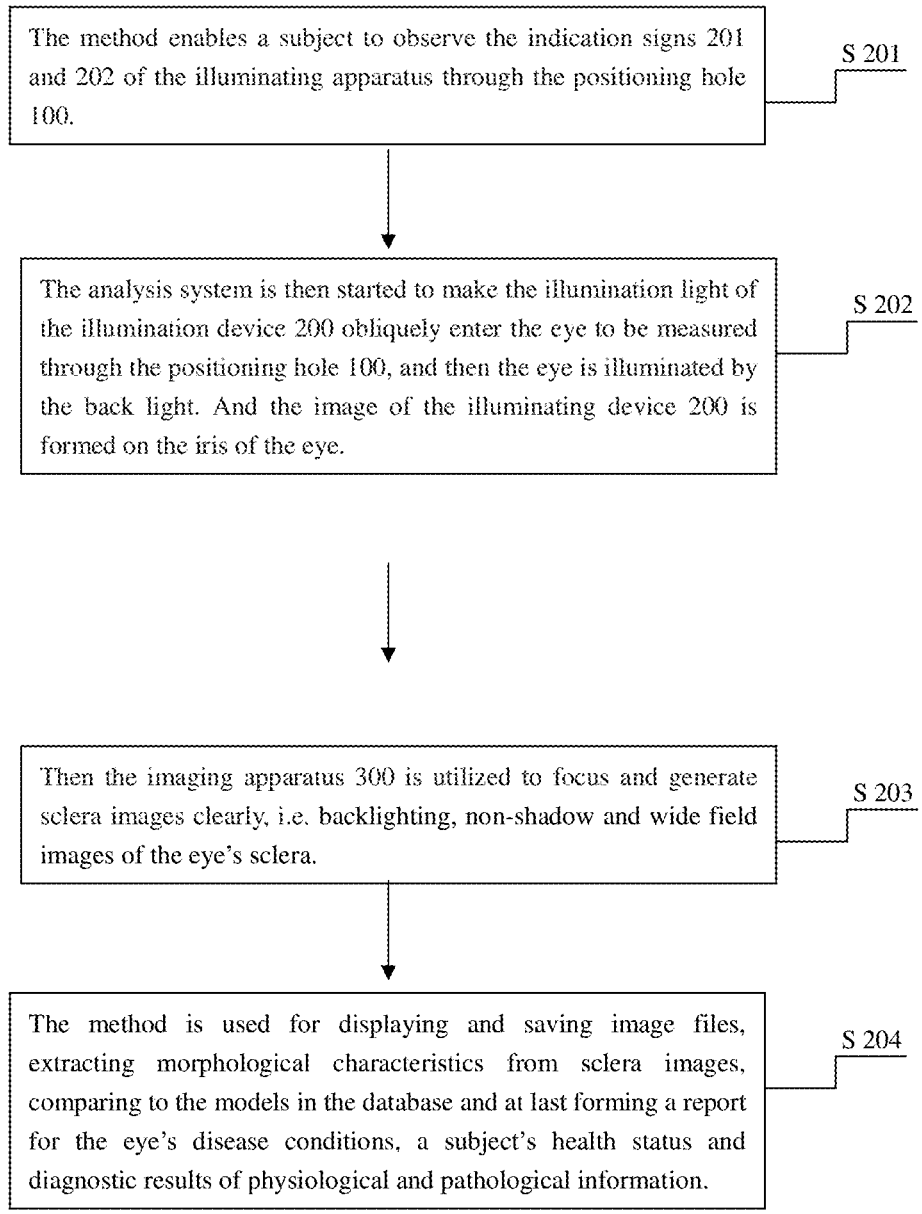
FIG. 6 shows another exemplary method for assessing a human health or disease status based on a non-shadow image of a sclera of the human subject, according to one aspect of the present disclosure.
Figure 7:
FIG. 7 shows an exemplary device according to one aspect of the present disclosure.

Also provided herein, in one aspect, is an method of on-body analysis for human health status based on non-shadow imaging of the eye's sclera, as shown in FIG. 6. In one aspect, the method comprises steps S201-S204. In one aspect, step S201 comprises having a subject to observe the indication signs 201 and 202 of the illuminating apparatus through the positioning hole 100. In one aspect, step S202 comprises guiding illumination light of the illumination device 200 obliquely through the positioning hole 100 to enter the eye to be measured. In another aspect, the method comprises illuminating the eye, which then reflects the light to be captured during imaging of the sclera. In another aspect, the illuminating device 200 illuminates the eye obliquely in the opposite direction of which the eye is looking, so that the image of the illuminating device 200 is formed on the iris of the eye. In one aspect, step S203 comprises using the imaging apparatus 300 to focus and generate a sclera image clearly, which in one aspect is a non-shadow and wide-field image of the eye's sclera. In one aspect, step S204 comprises saving image files, extracting morphological characteristics from sclera images, comparing to the models in the database, and/or forming a report for the eye's disease conditions, a subject's health status, a diagnostic result, and/or physiological and pathological information.

In any of the preceding embodiments, the on-body analysis system and methods provided herein can be for assessing human health status based on non-shadow imaging of sclera, or whites, of one or both eyes. In one aspect, the system comprises a positioning hole 100, illuminating apparatus 200, and/or an imaging apparatus 300. When a described analysis system is forming images of a sclera, the analysis system is first started to make the illumination light of the illumination device 200 obliquely enter the eye to be measured through the positioning hole 100, and then the eye is illuminated by the back light (light reflected from the eye). In one aspect, the subject observes the indication signs 201 and 202 of the illuminating apparatus through the positioning hole 100, thus the illuminating device 200 illuminates the eye obliquely in the opposite direction (back light) of the direction in which the eye is looking, so that the image of the illuminating device 200 is formed on the iris of the eye. In one aspect, the imaging apparatus 300 is utilized to generate a sclera image, which is a non-shadow and wide-field images of the eye's sclera. In another aspect, a processing apparatus 600 is used for saving image files, extracting morphological characteristics from sclera images, comparing to the models in the database, and/or forming a report for the eye's disease conditions, a subject's health status, and/or a diagnostic result of physiological and/or pathological information.

In any of the preceding embodiments, the device or system can perform wide-field and non-shadow and one-time imaging with only one camera without moving camera position or image reconstruction. In one aspect, it only takes a short time to obtain the images. In one aspect, the illuminating method uses light passing through a positioning hole obliquely to illuminate the testing eye, such that the image of the illuminating apparatus 200 itself is formed on the eye's iris instead of on the sclera. Image of the light source on the sclera affects the image quality of the sclera and should be avoided or reduced. In one aspect, the device or method herein does not generate reflection of the illuminating apparatus 200 on the sclera, which improves the quality of sclera imaging. In a further aspect, the system utilizes the sclera images to obtain information of eye diseases and to predict the physiological and pathological changes in the health status of subject or diagnostic results, which can provide helpful information for medical diagnosis.

Additional embodiments are provided below to further illustrate the present disclosure.

Embodiment 1: An on-body analysis system for assessing human health states, wherein the system takes non-shadow imaging of sclera, or whites, of one or both eyes, and finds the a feature of sclera for analyzing a physiological and/or pathological condition, wherein the system comprises:

a positioning hole for positioning an eye to carry out the operation with the system;

an illuminating apparatus for lighting, which is located on the opposite side of the eye to be tested, wherein light from the illuminating apparatus passes through the positioning hole to obliquely illuminate the eye, wherein the image of the illuminating apparatus itself is formed on the eye's iris instead of on the sclera of the eye;

an imaging apparatus used to take backlighting, non-shadow, and wide-field image of the eye's sclera;

a processing apparatus, connected to the imaging apparatus, for saving image files, extracting morphological characteristics from sclera images, comparing to the models in the database, and/or forming a report for the eye's disease conditions, a subject's health state, and/or a diagnostic or prognostic result, wherein the typical morphological characteristics and the corresponding diseases and pathological conditions are saved in the database in advance.

Embodiment 2: The analysis system described in Embodiment 1, which further comprises a display device, which is connected to the system's imaging apparatus, wherein the display device displays one or more images, morphological characteristics of sclera, the eye's disease conditions, a subject's health state assessment, and/or a diagnostic or prognostic result.

Embodiment 3: The analysis system described in Embodiment 1, wherein the morphological characteristics of sclera obtained by the analysis system comprise characteristics of colors, veins, and/or sclera surface.

Embodiment 4: The analysis system described in Embodiment 1, which is utilized for controlling the operation status of the illuminating apparatus and/or imaging apparatus.

Embodiment 5: The analysis system described in Embodiment 1, wherein the illuminating apparatus of the analysis system comprises one or more such as four illuminating units, which are located right, left, up, and down to the positioning hole, in order to facilitate obtaining four-direction backlighting, non-shadow and wide field images of sclera when the eyeball moves in those four directions.

Embodiment 6: The analysis system described in Embodiment 5, wherein the illuminating apparatus further comprises one or more signs beside the illuminating units, wherein each sign is on the near side of an illuminating unit to the positioning hole, as to indicate view directions and the sequence of different directions and also help fully expose the sclera.

Embodiment 7: The analysis system described in Embodiment 5, wherein the one or more illuminating units comprise one or more non-shadow bulbs, one or more filament lamps, one or more low pressure mercury lamps, one or more LEDs, and/or one or more lasers, or wherein the light that the illuminating units emit is polychromatic light or monochromatic light.

Embodiment 8: The analysis system described in Embodiment 1, wherein the positioning hole is a hole with a shape of a circle, an oval or a ring, and optionally comprises two left-right symmetric eye positioning surfaces and/or two up-down symmetric holes to flip eyelids.

Embodiment 9: The analysis system described in Embodiment 1, wherein the described imaging apparatus comprises one or more lens and/or one or more sensor chips, optionally wherein the lenses are used to send the light of an image to the sensing chip, and optionally wherein the sensor chip is for receiving the light of images on its surface and to generate images.

Embodiment 10: The analysis system described in Embodiment 9, wherein the analysis system comprises a focusing device connected to the lenses, which is used to adjust the lens to generate a sclera image or images on the sensor chip.

Embodiment 11: An on-body analysis method for assessing human health states using the analysis system described in any of Embodiments 1-10, wherein the method is used to take non-shadow imaging of a sclera, or whites, of one or both eyes and/or identify one or more features of the sclera for analyzing a physiological and/or pathological condition, wherein the method optionally comprises:
  starting the analysis system such that the illuminating apparatus generates a light, which can pass through a positioning hole to obliquely illuminate the testing eye, wherein the image of the illuminating apparatus itself is formed on the eye's iris instead of on the sclera;
  having the subject observe the illuminating apparatus through the positioning hole, such that the illuminating device illuminates the eye in the opposite direction (back light) of the way the eye is looking;
  using an imaging apparatus for generating a backlighting, non-shadow, wide field image of the sclera;
  using a processing apparatus for saving image files, extracting morphological characteristics from sclera images, comparing to the models in the database, and/or forming a report for the eye's disease conditions, a subject's health state, or a diagnostic or prognostic result.

Embodiment 12: The method according to Embodiment 11, wherein the extracted morphological characteristics of sclera images are pretreated with edge energy value correction algorithm to ensure the integrity of sclera area, the method comprising:
  identifying an initial matched mask for a sclera image by identifying the cutoff threshold values of the S and V channels in the HSV space before finding the white area and black area's locations of a sclera image, using the software's corrosion operation, removing the black area to obtain a local sclera image which is smaller than the whole sclera, as the described initial mask;
  treating a sclera image with gray-scale processing, for example, according to the gray-scale processing formula (I):

$$I = \min(255, (V + 100 \times fgb)) \times (\sim fv) \times ((1.5 - GB)^2 + 0.2) \qquad (I),$$

wherein I is the final grey-scale image; V represents the image in the V channel of the HSV space, i.e., the grey-scale image under a normal condition; fv represents the extracted edge image after treating the V channel image with a discrete first-order difference; ~fv represents the opposite version of the image fv; and fgb represents the image after edge extracting on a GB image, and wherein the GB image is defined in formula (II):

$$GB = \frac{((G - 1.05 \times B) - \min(G - 1.05B))}{\max(G - 1.05 \times B)}, \qquad (II)$$

wherein G and B represent the G channel and the B channel of a regular RGB color space, respectively, wherein in formula (I) and formula (II), fv ensures the final grey image's edge can stay at the right place within the sclera image area; $((1.5-GB)^2+0.2)$ can improve the difference or contrast between the sclera and the skin; and $+100 \times fgb$ can remove the influence of the skin's white outer edge in order to increase the probability for the edge to stay at the right place;

performing an energy bias correction using the initial mask obtained in the first step and the grey image obtained in the second step to calculate the curve's energy, for example, by using an eight-close-area method, wherein $I_{inside}$ and $I_{outside}$ are set as the average intensity of the inside and outside of the curve, respectively, and the energy of the curve is defined as E, which is calculated by using formula (III):

$$E = -\frac{1}{2}(I_{inside} - I_{outside})^2 \qquad (III),$$

wherein the energy bias correction on the gray-scale image is calculated by formula (IV):

$$\Delta E = E_{energy} + \alpha \times E_{curve} + b \qquad (IV),$$

wherein $E_{energy}$ refers to the energy of the initial mask's edge curve; $E_{curve}$ refers to the energy of the grey-scale image's edge curve after expanding the initial mask within the sclera area; α refers to the constant for the degree of mask edge's smoothness, and b refers to an empirical bias constant; wherein b can be adjusted in order to generate an outward pushing force to push the initial mask's edge to move outward quickly until when the edge reaches the original image's edge and ΔE=0, whereby the step serves the purpose of correcting the edge bias for the sclera image.

Embodiment 13: The method according to Embodiment 11 or Embodiment 12, wherein the analysis method further comprises displaying the morphological characteristics of sclera images and diagnostic results, wherein the morphological characteristics of sclera images comprise characteristics of colors, veins, and/or sclera surface, and wherein the diagnostic results comprise the eye's disease/health condition, a subject's health state assessment, and/or a diagnostic or prognostic result.

The invention claimed is:

1. A device for analyzing a sclera of a subject, comprising:
   a member comprising a positioning aperture for engaging an eye of a subject on one side of the positioning aperture, wherein the positioning aperture is on an imaginary plane and has a center; and
   a light source on the opposite side of the positioning aperture from the eye, wherein an imaginary line connecting the light source and the center of the positioning aperture intersects the plane at an angle of less than 90 degrees,
   wherein light from the light source, through the positioning aperture, obliquely illuminates the eye such that the reflection image of the light source is substantially outside of the sclera of the eye, whereby a sclera image is captured substantially without capturing the reflection image of the light source.

2. The device of claim 1, wherein the reflection image of the light source is completely outside of the sclera of the eye, and the sclera image is captured without capturing any part of the reflection image of the light source.

3. The device of claim 1, wherein the angle is less than about 80 degrees, about 70 degrees, about 60 degrees, or about 50 degrees.

4. The device of claim 1, wherein the angle is less than about 45 degrees, about 40 degrees, about 35 degrees, about 30 degrees, about 25 degrees, about 20 degrees, about 15 degrees, about 10 degrees, or about 5 degrees.

5. The device of claim 1, wherein all or part of the reflection image of the light source is on the iris of the eye, for example, at least about 50%, about 60%, about 70%, about 80%, about 90%, about 95%, or about 99% of the area of the reflection image is on the iris of the eye, while less than about 50%, about 40%, about 30%, about 20%, about 10%, about 5%, or about 1% of the area of the reflection image is on the sclera of the eye.

6. The device of claim 1, further comprising an imaging member for imaging the sclera of the eye, wherein the sclera image is a non-shadow, wide-field image.

7. The device of claim 1, further comprising a processing member configured to connect to the imaging member, wherein the processing member stores the sclera image, extract a feature of the sclera image, compares the extracted feature with a reference or model in a database, and/or generates report of a health/disease status of the eye, a health/disease status of another organ or tissue of the subject, a physiological or pathological indicator of the subject, an overall health/disease status of the subject, and/or a diagnostic or prognostic result.

8. The device of claim 7, wherein the feature of the sclera image is a morphological feature and the database comprises one or more sclera morphological features known to be associated with a healthy individual, a particular human population, and/or a disease or condition.

9. The device of claim 1, further comprising a display member configured to connect to the imaging member and/or the processing member, wherein the display member is configured to display the subject's sclera image, one or more features of the sclera image, a health/disease status of the eye, a health/disease status of another organ or tissue of the subject, a physiological or pathological indicator of the subject, an overall health/disease status of the subject, and/or a diagnostic or prognostic result.

10. The device of claim 1, wherein the sclera of the subject comprises one or more features, such as morphological features selected from the group consisting of a color feature, a blood vessel feature, and a surface morphology feature.

11. The device of claim 1, wherein the device further comprises an imaging member and a processing member, and the processing member controls the working status of the light source and/or the imaging member.

12. The device of claim 1, wherein the device comprises at least two, at least three, or at least four light sources, and wherein the four light sources are distributed to the left side, right side, upper side, and lower side of the positioning aperture, in order to facilitate exposure of the sclera for non-shadow and wide-field imaging when the eye turns to the left side, right side, upper side, and lower side, respectively.

13. The device of claim 1, further comprising one or more signs for the light source in order to facilitate exposure of the sclera for non-shadow and wide-field imaging when the eye turns to view the one or more signs.

14. The device of claim 1, wherein the light source comprises a non-shadow bulb, a filament lamp, a mercury lamp, a LED (light-emitting diode), a laser-emitting device, or a combination thereof, and wherein the light source emits a polychromatic light, a monochromatic light, a narrow-band light, or white light.

15. The device of claim 1, wherein the positioning aperture comprises an opening of a round, oval, ring, or eclipse shape, and comprises one or two openings for lifting or flipping the upper and/or the lower eyelid.

16. The device of claim 1, further comprising one or more lenses and/or one or more sensor chips, wherein the one or more lenses transmit light from the eye onto the one or more sensor chips, and the one or more sensor chips receive and convert light on the surface to one or more images.

17. The device of claim 1, further comprising one or more focusing member for adjusting the position of the one or more lenses, in order to form a good quality image of the sclera on the one or more sensor chips.

18. A device for analyzing a sclera of a subject, comprising:
    a member comprising a positioning aperture for engaging an eye of a subject on one side of the positioning aperture, wherein the positioning aperture comprises two horizontally symmetric eye positioning surfaces and two vertically symmetric holes for flipping the eyelids; and
    a light source on the opposite side of the positioning aperture from the eye, wherein an imaginary line connecting the light source and the center of the positioning aperture intersects the positioning aperture at an angle of less than 90 degrees,
    wherein light from the light source, through the positioning aperture, obliquely illuminates the eye such that the reflection image of the light source is completely outside of the sclera of the eye, whereby a sclera image is captured without capturing any part of the reflection image of the light source.

19. A method of analyzing a sclera of a subject, comprising using the device of claim 18 to obtain and analyze a non-shadow, wide-field image of the sclera.

20. The method of claim 19, wherein the image of the sclera is processed using an algorithm, the method comprising:
    (1) identifying an initial matched mask for a sclera image by identifying the cutoff threshold values of the S and V channels in the HSV space before finding the white area and black area's locations of a sclera image, using the software's corrosion operation, removing the black area to obtain a local sclera image which is smaller than the whole sclera, as the described initial mask;

(2) treating a sclera image with gray-scale processing, for example, according to the gray-scale processing formula (I):

$$I=\min(255, (V+100 \times fgb)) \times (\sim fv) \times ((1.5-GB)^2+0.2) \quad \text{(I)},$$

wherein I is the final grey-scale image; V represents the image in the V channel of the HSV space, i.e., the grey-scale image under a normal condition; fv represents the extracted edge image after treating the V channel image with a discrete first-order difference; ~fv represents the opposite version of the image fv; and fgb represents the image after edge extracting on a GB image, and wherein the GB image is defined in formula (II):

$$GB = \frac{((G-1.05 \times B) - \min(G-1.05B))}{\max(G-1.05 \times B)}, \quad \text{(II)}$$

wherein G and B represent the G channel and the B channel of a regular RGB color space, respectively, wherein in formula (I) and formula (II), fv ensures the final grey image's edge can stay at the right place within the sclera image area; $((1.5-GB)^2+0.2)$ can improve the difference or contrast between the sclera and the skin; and $+100 \times fgb$ can remove the influence of the skin's white outer edge in order to increase the probability for the edge to stay at the right place; and (3) performing an energy bias correction using the initial mask obtained in the first step and the grey image obtained in the second step to calculate the curve's energy, for example, by using an eight-close-area method, wherein $I_{inside}$ and $I_{outside}$ are set as the average intensity of the inside and outside of the curve, respectively, and the energy of the curve is defined as E, which is calculated by using formula (III):

$$E=-\tfrac{1}{2}(I_{inside}-I_{outside})^2 \quad \text{(III)},$$

wherein the energy bias correction on the gray-scale image is calculated by formula (IV):

$$\Delta E = E_{energy} + \alpha \times E_{curve} + b \quad \text{(IV)},$$

wherein $E_{energy}$ refers to the energy of the initial mask's edge curve; $E_{curve}$ refers to the energy of the grey-scale image's edge curve after expanding the initial mask within the sclera area; α refers to the constant for the degree of mask edge's smoothness, and b refers to an empirical bias constant; wherein b can be adjusted in order to generate an outward pushing force to push the initial mask's edge to move outward quickly until when the edge reaches the original image's edge and ΔE=0, whereby the step serves the purpose of correcting the edge bias for the sclera image.

21. The method of claim 20, wherein the analysis method further comprises displaying a morphological feature of the sclera image and/or a diagnostic or prognostic result, wherein the morphological feature comprises a color feature, a vein feature, and/or a surface morphology feature of the sclera, and wherein the diagnostic or prognostic result comprises a disease/health condition of the eye, and/or a health state assessment of the subject.

22. A method of analyzing a sclera of a subject, comprising using the device of claim 18 to obtain and analyze a non-shadow, wide-field image of the sclera.

* * * * *